(12) United States Patent
Greasley et al.

(10) Patent No.: US 12,121,517 B2
(45) Date of Patent: *Oct. 22, 2024

(54) COMBINATION OF ZIBOTENTAN AND DAPAGLIFLOZIN FOR THE TREATMENT OF ENDOTHELIN RELATED DISEASES

(71) Applicant: AstraZeneca AB, Södertälje (SE)

(72) Inventors: Peter Greasley, Mölndal (SE); Christine Ahlström, Mölndal (IL); Stanko Skrtic, Mölndal (SE); Robert Menzies, Mölndal (SE); Anne-Kristina Mercier, Mölndal (SE); Mikael Sunnåker, Mölndal (SE)

(73) Assignee: ASTRAZENECA AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/213,601

(22) Filed: Jun. 23, 2023

(65) Prior Publication Data

US 2023/0364077 A1 Nov. 16, 2023

Related U.S. Application Data

(63) Continuation of application No. 17/371,162, filed on Jul. 9, 2021, now Pat. No. 11,730,735.

(60) Provisional application No. 63/196,793, filed on Jun. 4, 2021, provisional application No. 63/050,147, filed on Jul. 10, 2020.

(51) Int. Cl.
*A61K 31/497* (2006.01)
*A61K 31/7034* (2006.01)
*A61P 13/12* (2006.01)

(52) U.S. Cl.
CPC ........ *A61K 31/497* (2013.01); *A61K 31/7034* (2013.01); *A61P 13/12* (2018.01)

(58) Field of Classification Search
CPC .... A61K 31/497; A61K 31/7034; A61P 13/12
See application file for complete search history.

(56) References Cited

U.S. PATENT DOCUMENTS

| | | | |
|---|---|---|---|
| 8,865,650 B2 | 10/2014 | Roden et al. | |
| 8,962,675 B1 | 2/2015 | Gong et al. | |
| 10,016,393 B2 | 7/2018 | Huang et al. | |
| 10,919,881 B2 | 2/2021 | Bolli et al. | |
| 11,730,735 B2 * | 8/2023 | Greasley | A61P 13/12 514/255.05 |
| 2021/0338648 A1 | 11/2021 | Hoegstedt | |

FOREIGN PATENT DOCUMENTS

| | | |
|---|---|---|
| WO | WO 2019/106066 | 6/2019 |
| WO | WO 2020/070539 | 4/2020 |
| WO | WO 2021/207723 | 10/2021 |

OTHER PUBLICATIONS

Breyer, M. D. & Susztak, K., "Developing Treatments for Chronic Kidney Disease in the 21st Century," Seminars in Nephrology, 36(6):436-447 (2016).
Lytvyn, Y. et al., "The New Biology of Diabetic Kidney Disease-Mechanisms and Therapeutic Implications," Endocrine Reviews, 41(2):202-231 (2020).
Muskiet M. et al., "New pharmacological strategies for protecting kidney function in type 2 diabetes," The Lancet Diabetes & Endocrinology, 7(5):397-412 (2019).
Raina, R. et al., "The Role of Endothelin and Endothelin Antagonists in Chronic Kidney Disease," Kidney Diseases, 6(1):22-34 (2019).
International Search Report for PCT/12021/056177 dated Sep. 27, 2021, 4 pages.
Stern Edward et al: "Evaluation of the Highly Selective Endothelin a Receptor Antagonist Zibotentan in Systemic Sclerosis Associated Chronic Kidney Disease", Nov. 10, 2019 (Nov. 10, 2019), pp. 1-3 Retrieved from the Internet: URL:https://acrabstracts.org/abstracl/evaluation-of-the-highly-selective-endothelina- eceptor-antagonist-zibotentan-in-systemic-sclerosis-associated-chronic-kidney-disease.
Stern E et al: "Evaluation of the endothelin a receptor antagonist zibotentan in systemic sclerosis-associated Ckd", Journal of the American Society of Nephrology 2019 American Society of NEPHROLOm NLD, vol. 30, 2019, 3 pages.
Heerspink, Hiddo JL et al., "New Insights from SONAR indicate adding sodium glucose co-transporter 2 inhibitors to □n endothelin receptor antagonist mitigates fluid retention," Kidney International, 99: 346-349 (2021).
Davenport, AP et al., "Endothelin," Pharmacol Rev, 68:357-418 (Apr. 2016).
Fernandez-Fernandez, Beatriz, "Canagliflozin and Renal events in diabetes with Established Nephropathy Clinical Evaluation and Study of Diabetic Nephropathy with Atrasentan: what was learned about the treatment of diabetic kidney disease with canagliflozin and atrasentan?" Clinical Kidney Journal, 12(3): 313-321 (2019).
Heerspink, Hiddo JL et al., Baseline characteristics and enrichment results from the SONAR trial, Diabetes Obes Metab., 20: 1829-1835 (2018).
Heerspink, Hiddo JL et al., Atrasentan and renal events in patients with type 2 diabetes and chronic kidney disease SONAR): a double blind randomized, placebo-controlled trial, The Lancet, 393: 1937-1947 (May 2019).

* cited by examiner

*Primary Examiner* — Timothy R Rozof
(74) *Attorney, Agent, or Firm* — Finnegan, Henderson, Farabow, Garrett & Dunner, LLP

(57) ABSTRACT

The present disclosure relates to the endothelin receptor antagonist (ERA) zibotentan in combination with the sodium-dependent glucose cotransporter 2 (SGLT-2) inhibitor dapagliflozin for use in the treatment of certain endothelin related diseases.

21 Claims, 9 Drawing Sheets

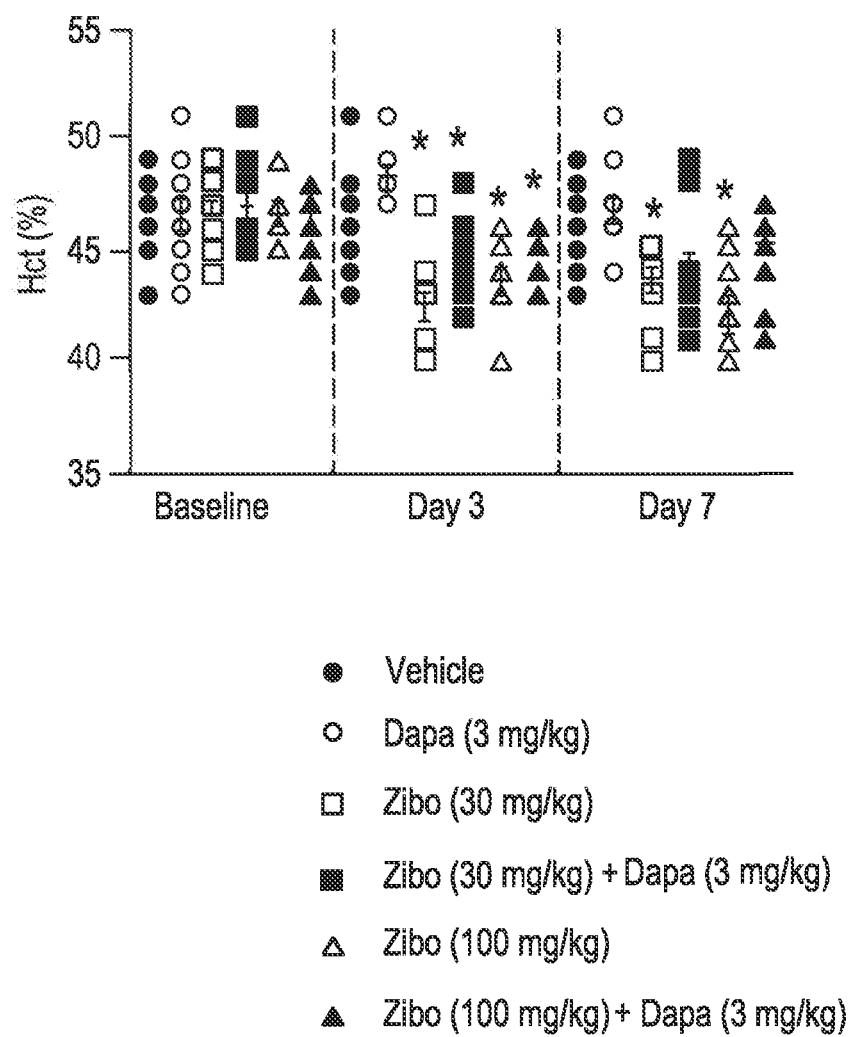

FIG. 10

| | Dapagliflozin No. of participants/total no. | Placebo No. of participants/total no. | Dapagliflozin Events/100 patient-years | Placebo Events/100 patient-years | | Hazard Ratio (95% CI) | P-value for Interaction |
|---|---|---|---|---|---|---|---|
| Regression to UACR <300 mg/g* | | | | | | | |
| Overall | 638/1913 | 424/1947 | 33.4 | 21.8 | | 1.81 (1.60, 2.05) | |
| With type 2 diabetes | 464/1288 | 282/1310 | 36.0 | 21.5 | | 2.06 (1.78, 2.39) | 0.001 |
| Without type 2 diabetes | 174/625 | 142/637 | 27.8 | 22.3 | | 1.33 (1.07, 1.66) | |
| Progression to UACR ≥3000 mg/g† | | | | | | | |
| Overall | 95/1909 | 215/1911 | 5.0 | 11.3 | | 0.41 (0.32, 0.52) | |
| With type 2 diabetes | 71/1251 | 169/1251 | 5.7 | 13.5 | | 0.39 (0.29, 0.51) | 0.40 |
| Without type 2 diabetes | 24/658 | 46/660 | 3.6 | 7.0 | | 0.50 (0.30, 0.82) | |

COMBINATION OF ZIBOTENTAN AND DAPAGLIFLOZIN FOR THE TREATMENT OF ENDOTHELIN RELATED DISEASES

CROSS REFERENCES TO RELATED APPLICATIONS

This application is a continuation of U.S. application Ser. No. 17/371,162, filed Jul. 9, 2021, which claims the benefit of priority of U.S. Provisional Patent Application No. 63/196,796, filed on Jun. 4, 2021, and U.S. Provisional Patent Application No. 63/050,147, filed on Jul. 10, 2020, all of which are incorporated herein by reference in their entirety.

TECHNICAL FIELD

The present disclosure relates to the endothelin receptor antagonist (ERA) zibotentan in combination with the sodium-dependent glucose cotransporter 2 (SGLT-2) inhibitor dapagliflozin for use in the treatment of certain endothelin related diseases.

BACKGROUND

Endothelin-1 (ET-1) is a potent vasoconstrictive peptide. ET-1, modulated by endothelin A and B receptors ($ET_A$ and $ET_B$), is a highly potent systemic vasoconstrictor and driver of renal disease progression. In chronic kidney disease (CKD) ET-1 levels increase with urinary albumin creatinine ratio (UACR) and severity of renal functional impairment (Grenda et al., *Nephrol Dial Transplant.* 2007; 22(12): 3487-3494; Kohan *Am J Kidney Dis.* 1997; 29(1): 2-26). The pathological effects of ET-1 including proteinuria, vasoconstriction and inflammation are thought to be predominantly driven by the endothelial A ($ET_A$) receptor (Goddard et al., *Circulation.* 2004; 109(9): 1186-1193). $ET_A$ antagonists have demonstrated kidney protective effects. In Diabetic Kidney Disease (DKD) a 30% reduction in urinary albumin to creatinine ratio (UACR) has been demonstrated (Heerspink et al., *Diabetes Obes Metab.* 2018; 20(8): 1829-1835; Heerspink et al., *Lancet* 2019; 393(10184): 1937-1947). However, clinical development with $ET_A$ receptor antagonist have been limited due to issues of fluid retention and hospitalization for heart failure (Heerspink et al., *Lancet* 2019; 393(10184): 1937-1947). Zibotentan is a potent $ET_A$ receptor antagonist developed by for treatment of prostate cancer but was stopped in 2011 due to insufficient efficacy in Phase 3 and a 17% increase in incidence of peripheral oedema compared to placebo.

SGLT-2 inhibitors result in osmotic diuretics as a result of glucosuria, increasing urine volume and decreasing volume overload largely independent of changes in systemic sodium load. SGLT-2 inhibitors block glucose reabsorption in the kidney, increase glucose excretion, and lower blood glucose concentration. In addition to this well characterized mode of action, SGLT-2 inhibitors reduce blood pressure, decrease vascular stiffness, improve endothelial function, and have anti-inflammatory and anti-fibrotic properties resembling those of ERAs (H. J. Heerspink et al., Circulation (2016), 134(10): 752-772). SGLT2 inhibitors have proven efficacy in DKD (Stephens et al., *Diabetes Obes Metab.* 2020; 22 Suppl 1:32-45). Dapagliflozin is being investigated for its efficacy in CKD in the DAPA-CKD trial which was recently stopped early due to overwhelming efficacy. Posthoc analysis of the SONAR trial presented at American Society of Nephrology's annual Kidney Week meeting in Washington, DC, 2019 showed that in a subset of DKD patients (n=14) taking both the $ET_A$ antagonists atrasenetan and a SGLT2 inhibitor increased UACR reduction compared to atrasenetan alone and reduced weight gain caused by atrasentan, a surrogate for fluid retention.

Zibotentan, N-(3-methoxy-5-methylpyrazin-2-yl)-2-[4-(1,3,4-oxadiazol-2-yl)phenyl]pyridine-3-sulfonamide, has the chemical structure of formula I

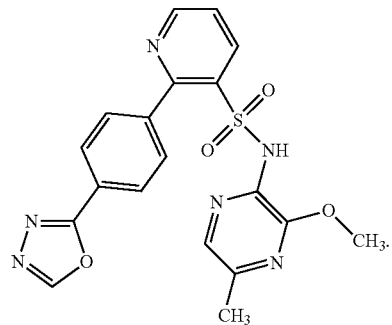

Zibotentan, also referred to as ZD4054, has been disclosed as an entothelin receptor antagonist in WO1996040681 along with details on the chemical synthesis of zibotentan. The specific inhibition of the endothelin A receptor with zibotentan has been reported by Morris et al., British Journal of Cancer (2005), 92, 2148-2152.

Dapagliflozin, (1S)-1,5-anhydro-1-{4-chloro-3-[(4-ethoxyphenyl)methyl]phenyl}-D-glucitol, has the chemical structure of formula II

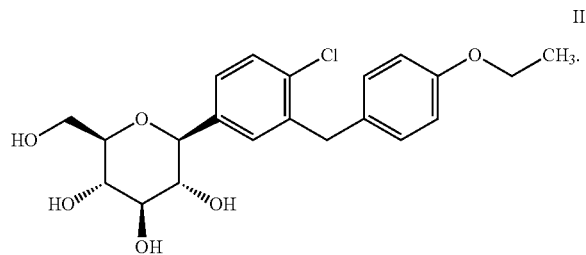 [SMILES: CCOc1ccc(Cc2cc([C@@H]3O[C@H](CO)[C@@H](O)[C@H](O)[C@H]3O)ccc2Cl)cc1]

Dapagliflozin is a potent, highly selective, and orally active inhibitor of human renal sodium-dependent glucose transporter 2 (SGLT2) (SGLT2i) that has been approved to improve glycemic control in adults with type 2 diabetes mellitus (as an adjunct to diet and exercise) and to reduce the risk of hospitalization for heart failure in adults with type 2 diabetes mellitus and established cardiovascular disease or multiple cardiovascular risk factors. Dapagliflozin has been disclosed in WO2003099836 along with details on the chemical synthesis.

When combining the specific inhibitor of the endothelin A receptor, zibotentan, with the SGLT-2 inhibitor dapagliflozin, the diuretic effect of dapagliflozin may be mitigated by the fluid retention side effect associated with the entothelin receptor antagonist zibotentan, hereby mitigating both risks associated with respective individual compounds.

In this specification, it is shown that dapagliflozin mitigates zibotentan driven hemodilution, where hemodilution is defined as reduced haematocrit concentration, and hence highlights the potential for a combination of zibotentan and dapagliflozin to demonstrate efficacy in the treatment of certain endothelin related diseases.

Endothelin-1, modulated by endothelin A and B receptors ($ET_A$ and $ET_B$), is a highly potent systemic vasoconstrictor and driver of renal disease progression.

$ET_A$ antagonist blockade improves renal function whereas $ET_B$ blockade is not preferred because $ET_B$ also clears circulating endothelin-1.

Endothelin related diseases are associated with an increase in vasoconstriction, proliferation or inflammation due to endothelin occurring in many cardio-renal-metabolic diseases. Examples of such endothelin related diseases are hypertension, coronary diseases, cardiac insufficiency, renal and myocardial ischemia, chronic kidney disease (CKD). In particular CKD associated with hypertension or diabetes (Diabetic Kidney Disease, DKD). An ERA might be beneficial in the treatment of peripheral arterial obliterant disease including diabetic arteriopathy by having acute (peripheral vasodilation) and chronic (vasodilation, improvement in vascular structure and modulation of sympathetic activity, antithrombotic, antiinflammatory) effects.

The mode of action of SGLT-2 leads to simultaneous inhibition of glucose and sodium uptake in the proximal tubules of the nephron, believed to result in a reset of the tubulo-glomerular feedback putatively causing the phenomenon of glomerular hyperfiltration. The efficacy of SGLT-2 inhibitors is believed to decrease with lower plasma glucose levels or a drop in glomerular filtration rate (GFR), thus, SGLT-2 inhibitors have an inherent low risk for developing hypoglycemia. In consequence, the properties of SGLT-2 inhibitors may open a pathway to treat HF including HFpEF even in non-diabetic patients (P. Martens et al., Curr Treat Options Cardio Med (2017), 19: 23).

A side effect associated with the pharmacological effects of SGLT-2 inhibitors is volume depletion/intravascular volume contraction, potentially leading to dehydration, hypovolemia, orthostatic hypotension, or hypotension. Thus, SGLT-2 inhibitors generally induce an increase in hematocrit (Hct) a marker of haemoconcentration and increased blood viscosity, a putative cause of vascular injury in a context of peripheral vascular disease.

Serium creatinine is increased and eGFR is decreased by the pharmological action of SGLT-2 inhibitors. Zibotentan, an ERA resulting in effective blockade of the $ET_A$ receptor, may be suited for the treatment of endothelin related diseases when prescribed in combination with dapagliflozin. When combining an ERA with an SGLT-2 inhibitor, the diuretic effect of such SGLT-2 inhibitor and its potential pharmacological action in reducing the risk of heart failure may be suitable to mitigate the most prominent side effects generally associated with ERAs such as fluid retention and potentially associated increased risk of congestive heart failure. Such combination treatment may result in pharmacological action on the disclosed endothelin related diseases, while maintaining a favourable side effect profile even at optimal efficacious dosages of zibotentan, potentially even at increased dosages of zibotentan when compared to maximum tolerated doses of zibotentan alone. Increased doses of zibotentan that may become accessible, e.g. due to mitigated side effects, when zibotentan is used in combination with dapagliflozin may allow to amplify the impact on diseases that are caused by deleterious effects of the endothelin paracrine system widely distributed in the organism. Such combination treatment may improve the benefit/risk ratio. ERAs have been described to decrease hematocrit (Hct) via hemodilution. Thus, zibotentan when used in combination with dapagliflozin may antagonize the most prominent side effects generally associated with SGLT-2 inhibitors such as hemoconcentration due to volume depleting effect. ERAs have been described to improve blood sugar levels by various mechanisms (increased blood flow, improvement of insulin signalling). Thus, zibotentan when used in combination with dapagliflozin may have additive, or even synergistic effects on blood sugar reduction.

In a first aspect, there is provided zibotentan for use in the treatment of Chronic Kidney Disease (CKD) in a human patient, wherein zibotentan is administered in combination with dapagliflozin.

In a further aspect, there is provided a method of treating Chronic Kidney Disease (CKD) in a human patient in need of such a treatment comprising administration to the human patient a therapeutically effective amount of zibotentan, wherein zibotentan is administered in combination with a therapeutically effective amount of dapagliflozin.

In a further aspect, there is provided the use of zibotentan in the manufacture of a medicament for the treatment of Chronic Kidney Disease (CKD) in a human patient, wherein zibotentan is administered in combination with dapagliflozin.

DESCRIPTION OF THE FIGURES

FIGS. 6A-6C show the effect of zibotentan, dapagliflozin and the combination on Hct in Example 1, Experiment 2. FIG. 6A shows a comparison of baseline, Day 3, and Day 7 results. FIG. 6B depicts results on Day 3, and FIG. 6C depicts results on Day 7.

FIG. 10 shows the regression and progression of UACR in patients with CKD stratified by diabetic status from the DAPA CKD Phase 3 trial.

DETAILED DESCRIPTION

Figure 1:
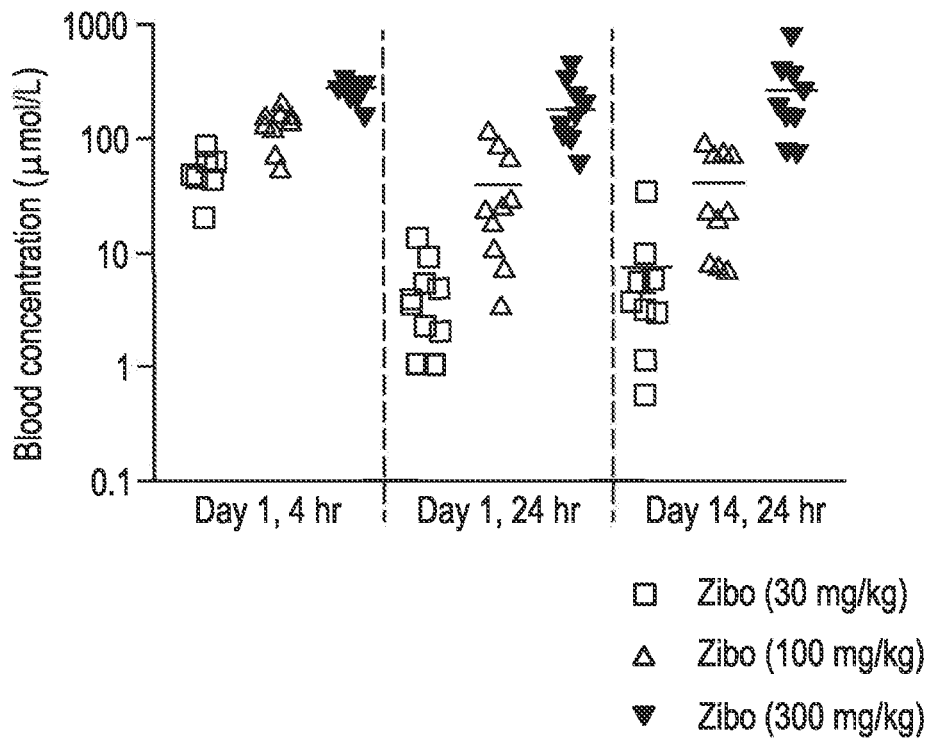
FIG. 1 shows the individual zibotentan blood concentrations in Example 1, Experiment 1 following oral administration of zibotentan.

In a first aspect, there is provided zibotentan for use in the treatment of Chronic Kidney Disease (CKD) in a human patient, wherein zibotentan is administered in combination with dapagliflozin.

In a further aspect, there is provided a method of treating Chronic Kidney Disease (CKD) in a human patient in need of such a treatment comprising administration to the human patient a therapeutically effective amount of zibotentan, wherein zibotentan is administered in combination with a therapeutically effective amount of dapagliflozin.

In a further aspect, there is provided the use of zibotentan in the manufacture of a medicament for the treatment of Chronic Kidney Disease (CKD) in a human patient, wherein zibotentan is administered in combination with dapagliflozin.

In certain embodiments, the Chronic Kidney Disease (CKD) is CKD of stages 1 to 4 as defined by the Kidney Disease Improving Global Outcomes (KDIGO) Guidelines.

In certain embodiments, the CKD is CKD of stages 2-3.

In certain embodiments, the CKD is CKD of stages 3-4.

In certain embodiments, the CKD is CKD of stage 4.

In certain embodiments, the CKD is CKD of stages 3a or 3b.

Zibotentan, N-(3-methoxy-5-methylpyrazin-2-yl)-2-[4-(1,3,4-oxadiazol-2-yl)phenyl]pyridine-3-sulfonamide, has the chemical structure of formula I

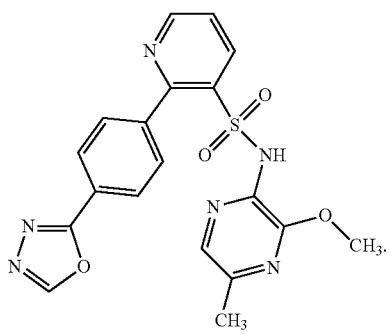

Zibotentan is also referred to as ZD4054.

In embodiments, zibotentan, or a pharmaceutically acceptable salt thereof, is administered once daily.

In embodiments, the total daily dose of zibotentan is about 10 mg.

In embodiments, the total daily dose of zibotentan is about 5 mg.

In embodiments, the total daily dose of zibotentan is about 1.5 mg.

In embodiments, the total daily dose of zibotentan is about 0.5 mg.

In embodiments, the total daily dose of zibotentan is about 0.25 mg.

In embodiments, zibotentan, or a pharmaceutically acceptable salt thereof, is in tablet form.

In embodiments, zibotentan, or a pharmaceutically acceptable salt thereof, is administered in the form of a pharmaceutical composition comprising one or more pharmaceutically acceptable excipients. In further embodiments, the composition comprises one or more pharmaceutical diluents, one or more pharmaceutical disintegrants or one or more pharmaceutical lubricants.

Dapagliflozin, (1S)-1,5-anhydro-1-{4-chloro-3-[(4-ethoxyphenyl)methyl]phenyl}-D-glucitol, has the chemical structure of formula II

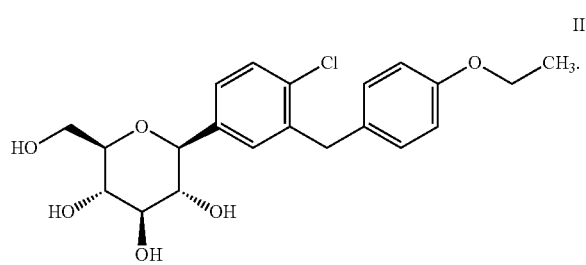 [SMILES: CCOc1ccc(Cc2cc([C@@H]3O[C@H](CO)[C@@H](O)[C@H](O)[C@H]3O)ccc2Cl)cc1]

In embodiments, dapagliflozin, or a pharmaceutically acceptable salt thereof, is administered once daily.

In at least one embodiment, dapagliflozin is in the form of a pharmaceutically acceptable solvate, mixed solvate, or complex. In some aspects provided herein, dapagliflozin is in the form of a non-crystalline solid. In some aspects provided herein, dapagliflozin is in the form of a crystalline solid. In some aspects provided herein, dapagliflozin is in the form of a (S)-propylene glycol ((S)-PG) solvate, which has the structure:

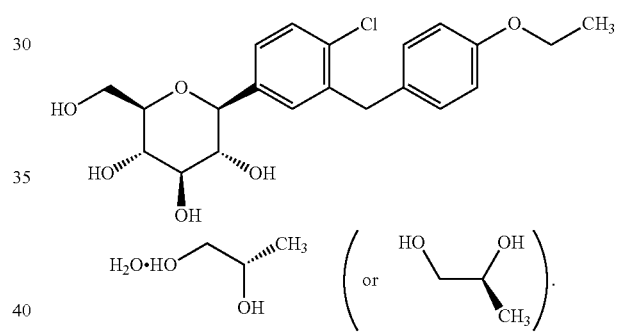

In at least one embodiment, dapagliflozin is in the form of a pharmaceutically acceptable solvate, mixed solvate, or complex. In some aspects provided herein, dapagliflozin is in the form of a non-crystalline solid. In some aspects provided herein, dapagliflozin is in the form of a crystalline solid.

In some aspects provided herein, the pharmaceutical compositions are administered to the patient orally. In some aspects provided herein, the pharmaceutical compositions are administered to the patient in a tablet form.

In some aspects provided herein, the pharmaceutical composition comprising dapagliflozin comprises a dose equivalent of about 2.5 mg/day to about 10 mg/day dapagliflozin is administered to the patient. In some aspects provided herein, the pharmaceutical composition comprising dapagliflozin comprises a dose equivalent of about 2.5 mg/day, about 5 mg/day, or about 10 mg/day dapagliflozin is administered to the patient. In some aspects provided herein, the pharmaceutical composition comprising dapagliflozin comprises a dose equivalent of about 5 mg/day dapagliflozin is administered to the patient once per day. In some aspects provided herein, the pharmaceutical composition comprising dapagliflozin comprises a dose equivalent of about 10 mg/day dapagliflozin is administered to the patient once per day.

In an aspect there is provided zibotentan for use in the treatment of CKD in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient.

In an aspect there is provided a method of treating CKD in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient.

In an aspect there is provided use of zibotentan in the manufacture of a medicament for the treatment of CKD in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient.

In an aspect there is provided zibotentan for use in reducing UACR in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing UACR in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for the reduction of UACR in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in reducing UACR to <300 mg/g in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing UACR to <300 mg/g in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for the reduction of UACR to <300 mg/g in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in decreasing the risk of progression to UACR to ≥3000 mg/g in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of decreasing the risk of progression to UACR to ≥3000 mg/g in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for decreasing the risk of progression to UACR to ≥3000 mg/g in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in reducing the risk of eGFR decline in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes. In some embodiments, the use reduces the risk of ≥30% decline in eGFR. In some embodiments, the use reduces the incidence of ≥40% decline in eGFR.

In an aspect there is provided a method of reducing the risk of eGFR decline in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes. In some embodiments, the method reduces the risk of ≥30% decline in eGFR. In some embodiments, the method reduces the incidence of ≥40% decline in eGFR.

In an aspect there is provided use of zibotentan in the manufacture of a medicament for reducing the risk of eGFR decline in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes. In some embodiments, the use reduces the risk of ≥30% decline in eGFR. In some embodiments, the use reduces the incidence of ≥40% decline in eGFR.

In an aspect there is provided zibotentan for use in reducing the risk of fluid retention (edema) in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes. In some embodiments, reduction in the risk of fluid retention (edema) may be measured by, for example, a decrease in Hct or increase in body weight.

In an aspect there is provided a method of reducing the risk of fluid retention (edema) in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes. In some embodiments, reduction in the risk of fluid retention (edema) may be measured by, for example, a decrease in Hct or increase in body weight.

In an aspect there is provided use of zibotentan in the manufacture of a medicament for reducing the risk of fluid retention (edema) in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes. In some embodiments, reduction in the risk of fluid retention (edema) may be measured by, for example, a decrease in Hct or increase in body weight.

In an aspect there is provided zibotentan for use in reducing total body water in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing total body water in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for reducing total body water in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in reducing blood pressure in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing blood pressure in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for reducing blood pressure in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in reducing the risk of blood pressure elevation in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing the risk of blood pressure elevation in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for reducing the risk of blood pressure elevation in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in reducing the incidence of a composite endpoint of ≥40% decline in eGFR, reaching end-stage kidney disease (ESKD), and cardiovascular or renal death in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing the incidence of a composite endpoint of >40% decline in eGFR, reaching end-stage kidney disease (ESKD), and cardiovascular or renal death in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for reducing the incidence of a composite endpoint of >40% decline in eGFR, reaching end-stage kidney disease (ESKD), and cardiovascular or renal death in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in reducing the incidence of reaching end-stage kidney disease (ESKD) in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing the incidence of reaching end-stage kidney disease (ESKD) in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for reducing the incidence of reaching end-stage kidney disease (ESKD) in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided zibotentan for use in reducing the incidence of cardiovascular or renal death in a human patient, comprising administering either separately, sequentially, or simultaneously: i) zibotentan and ii) dapagliflozin to the human patient. In further embodiments, the human patient is a CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided a method of reducing the incidence of cardiovascular or renal death in a human patient in need of such a treatment comprising administration to the human patient a therapeutically effective amount of zibotentan, wherein the treatment comprises the separate, sequential, or simultaneous administration of i) a therapeutically effective amount of zibotentan and ii) a therapeutically effective amount of dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In an aspect there is provided use of zibotentan in the manufacture of a medicament for reducing the incidence of cardiovascular or renal death in a human patient, wherein the treatment comprises the separate, sequential, or simultaneous administration of i) zibotentan and ii) dapagliflozin to the human patient. In further embodiments, the human patient is CKD human patient. In further embodiments, the human patient is CKD human patient classified as a stage 1-4 patient. In further embodiments, the human patient is CKD human patient classified as a stage 3-4 patient. In further embodiments, the human patient is CKD human patient classified as a stage 4 patient. In further embodiments, the human patient is CKD human patient classified as a stage 3a or 3b patient. In further embodiments, the human patient is CKD human patient classified as a stage 2-3 patient. In further embodiments, the human patient is a CKD human patient with Type 2 diabetes. In other embodiments, the human patient is a CKD human patient without Type 2 diabetes.

In any of the above aspects, the methods and uses thereof may also be relative to a human patient receiving at least one SGLT2-I (e.g., dapagliflozin, empagliflozin, canagliflozin, etc.) alone or in combination with at least one standard of care CKD agent. In such aspects, the standard of care CKD agent may be ACE-Is (e.g., captopril, enalapril, and lisinopril) and/or ARBs (valsartan, losartan, and irbesartan).

In any of the above aspects, the methods and uses thereof may be relative to the patient from baseline. In some embodiments, the methods and uses thereof may be relative to the patient from baseline compared to patients receiving at least one SGLT2-I alone or in combination with at least one standard of care CKD.

In an aspect there is provided a kit comprising:
a first pharmaceutical composition comprising zibotentan and a pharmaceutically acceptable carrier; and
a second pharmaceutical composition comprising dapagliflozin and a pharmaceutically acceptable carrier.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. Patients or subjects in need of treatment of treatment can include those diagnosed with CKD.

A "therapeutically effective amount" or "effective amount" refers to an amount of at least one compound of the present disclosure or a pharmaceutical composition comprising at least one such compound that, when administered to a patient, either as a single dose or as part of a series of doses, is effective to produce at least one therapeutic effect. Optimal doses may generally be determined using experimental models and/or clinical trials.

Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the patient. Patients may generally be monitored for therapeutic effectiveness using assays suitable for the disease, disorder and/or condition being treated or prevented, which assays will be familiar to those having ordinary skill in the art and are described herein. The level of a compound that is administered to a patient may be monitored by determining the level of the compound (or a metabolite of the compound) in a biological fluid, for example, in the blood, blood fraction (e.g., serum), and/or in the urine, and/or other biological sample from the patient. Any method practiced in the art to detect the compound, or metabolite thereof, may be used to measure the level of the compound during the course of a therapeutic regimen Alternatively, the pharmacologic and/or physiologic effect may be prophylactic, i.e., the effect completely or partially prevents a disease or symptom thereof. In this respect, the disclosed method comprises administering a "prophylactically effective amount" of a drug (e.g., zibotentan or a pharmaceutically acceptable salt, solvate, mixed solvate, complex, or prodrug thereof and dapagliflozin or a pharmaceutically acceptable salt, solvate, mixed solvate, complex, or prodrug thereof). A "prophylactically effective amount" refers to an amount effective, at dosages and for periods of time necessary, to achieve a desired prophylactic result (e.g., prevention of CKD or disease onset).

As used herein, the terms "subject" and "patient" are used interchangeably. In some aspects, the subject is a human.

As used herein, the term "end-stage kidney disease (EKSD)" refers to (i) having a sustained eGFR<15 mL/min/1.73m2, (ii) receiving chronic dialysis treatment, or (iii) receiving a renal transplant. In some embodiments, "sustained" refers to a confirmation of a similar eGFR measurement by a second eGFR test 3 months apart.

The terms "administer," "administering," "administration," and the like, as used herein, refer to methods that may be used to enable delivery of a drug, e.g., zibotentan or a pharmaceutically acceptable salt, solvate, mixed solvate, complex, or prodrug thereof and dapagliflozin or a pharmaceutically acceptable salt, solvate, mixed solvate, complex, or prodrug thereof, as described herein. Administration techniques that can be employed with the agents and methods described herein are found in e.g., Goodman and Gilman, *The Pharmacological Basis of Therapeutics*, current edition, Pergamon; and Remington's, *Pharmaceutical Sci-*

*ences*, current edition, Mack Publishing Co., Easton, Pa. In some aspects, zibotentan and dapagliflozin are administered orally.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

As used herein, the term "prodrug" refers to, for example, esters and carbonates that may be converted, for example, under physiological conditions or by solvolysis, to zibotentan or dapagliflozin. Thus, the term prodrug includes metabolic precursors of zibotentan or dapagliflozin that are pharmaceutically acceptable. The term prodrug also includes covalently bonded carriers that release zibotentan or dapagliflozin in vivo when such prodrug is administered to a patient. Non-limiting examples of prodrugs include esters and carbonates.

Various forms of prodrugs are known in the art. For examples of such prodrug derivatives, see: (1) Design of Prodrugs, edited by H. Bundgaard, (Elsevier, 1985) and Methods in Enzymology, Vol. 42, p. 309-396, edited by K. Widder, et al. (Academic Press, 1985); (2) A Textbook of Drug Design and Development, edited by Krogsgaard-Larsen and H. Bundgaard, Chapter 5 "Design and Application of Prodrugs", by H. Bundgaard p. 113-191 (1991); (3) H. Bundgaard, Advanced Drug Delivery Reviews, 8, 1-38 (1992); (4) H. Bundgaard, et al., Journal of Pharmaceutical Sciences, 77, 285 (1988); and (5) N. Kakeya, et al., Chem Pharm Bull, 32, 692 (1984).

It is understood that wherever aspects are described herein with the language "comprising," otherwise analogous aspects described in terms of "consisting of" and/or "consisting essentially of" are also provided. In this disclosure, "comprises," "comprising," "containing" and "having" and the like can mean "includes," "including," and the like; "consisting essentially of" or "consists essentially" are open-ended, allowing for the presence of more than that which is recited so long as basic or novel characteristics of that which is recited is not changed by the presence of more than that which is recited, but excludes prior art aspects.

Unless specifically stated or obvious from context, as used herein, the term "or" is understood to be inclusive.

As used herein, the terms "about" and "approximately," when used to modify a numeric value or numeric range, indicate that deviations of up to 10% above and down to 10% below the value or range remain within the intended meaning of the recited value or range. It is understood that wherever aspects are described herein with the language "about" or "approximately" a numeric value or range, otherwise analogous aspects referring to the specific numeric value or range (without "about") are also provided.

EXPERIMENTAL PROCEDURES

Example 1

The effect of dapagliflozin and zibotentan on haematocrit (Hct) concentration in male Wistar rats on 4% salt diet was investigated.

In Experiment 1, zibotentan was administered orally once daily at 30, 100 or 300 mg/kg for 14 days. On day 7, all three doses of zibotentan resulted in a significant decrease in Hct concentration compared to vehicle (p<0.05). On day 14 a significant decrease in Hct concentration compared to vehicle (p<0.05) was found for the higher doses of zibotentan (100 mg/kg and 300 mg/kg) but not for the lower dose (30 mg/kg).

In Experiment 2, Hct concentration was measured following 7 days administration of zibotentan (30 or 100 mg/kg) or dapagliflozin (3.0 mg/kg) alone or in combination in male Wistar rats fed a 4% salt diet. Zibotentan (30 or 100 mg/kg) significantly decreased Hct concentration. Co-administration of dapagliflozin (3.0 mg/kg) with zibotentan (30 mg/kg) resulted in a Hct concentration that was not significantly different from vehicle treated animals. Co-administration of dapagliflozin (3.0 mg/kg) with zibotentan (100 mg/kg) attenuated zibotentan's effect on Hct concentration as revealed by one way ANOVA, Post hoc Tukey's test (zibotentan −4.00±0.87 vs zibotentan+dapagliflozin −1.72±0.68, [#]p<0.05). Zibotentan did not impact dapagliflozin's effect on urine glucose excretion.

Materials and Methods

Formulation for zibotentan alone: Suspension in 30% (w/w) TEG 2% (w/w) EtOH 0.5% (w/w) HPMC 10000 cps 0.1% (w/w) Tween 80 67.4% purified water Formulation for dapagliflozin alone: Solution in 30% (w/w) TEG 2% (w/w) EtOH 0.5% (w/w) HPMC 10000 cps 0.1% (w/w) Tween 80 67.4% purified water Formulation for the combination of zibotentan and dapagliflozin: Suspension/solution in 30% (w/w) TEG 2% (w/w) EtOH 0.5% (w/w) HPMC 10000 cps 0.1% (w/w) Tween 80 67.4% purified water The study was divided in two experiments.

In the first experiment (Experiment 1), the effect of zibotentan on haematocrit (Hct) concentration was determined when zibotentan was administered peroral (p.o) QD for 14 days. Three days prior to first administration of study drug animals were randomized based on body weight (BW) into the following groups; 1) Vehicle 2) Zibotentan (30 mg/kg) 3) Zibotentan (100 mg/kg) 4) Zibotentan (300 mg/kg). Animals were weighed daily prior to dosing throughout the experiment. Blood samples (20 µL) for bioanalysis were taken at 4 and 24 hr after the first dose via the tail vein from conscious animals and 24 hr after the last dose via retroorbital route from anesthetized animals. Blood samples were collected via tail vein (100 μL) for Hct concentration and haemoglobin (Hb) measurements, on day 7 and on day 14, 1-2 hr after dosing. Twenty-four hour urine was collected for the measurement of urinary glucose, urine volume and electrolytes between doses nine and ten. Animals were terminated 24 hr after the last dose. On the day of termination, animals were anesthetized using 5% isoflurane, and blood was collected via the retroorbital route (in heparin-coated microvette, Sarsted) and centrifuged at 3,500 rpm at 4° C. for 10 minutes, plasma was collected and stored at −80° C. degrees prior to analysis. Animals were then euthanized by the removal of the heart. Both the heart and the kidneys were extracted and weighed. From the right kidney, a 4 mm thick slice of tissue was collected and fixed in 4% formaldehyde for subsequent histological analysis and a piece of cortical kidney tissue and heart tissue was collected for gene expression analysis.

In the second experiment (Experiment 2), the effect of zibotentan and dapagliflozin (alone or in combination) on Hct concentration and Hb was determined. Seventy-two animals were randomized on BW and Hct concentration, 2 to 3 days prior to administration of study drugs into the following groups; 1) Vehicle, 2) Zibotentan (30 mg/kg), 3) Zibotentan (100 mg/kg), 4) Dapagliflozin (3 mg/kg), 5) Zibotentan (30 mg/kg)+Dapagliflozin (3 mg/kg) and 6) Zibotentan (100 mg/kg)+Dapagliflozin (3 mg/kg). For practical reasons, the study was conducted in two consecutive slots with 36 animals (6/group) in each slot. Compounds were administered p.o. QD for seven days. Blood samples for bioanalysis were collected at 4 and 24 hr after the first dose and 24 hr after the final dose for Hct concentration and Hb analysis on day three and seven as described for exp.1. Twenty-four hour urine was collected between the third and fourth dose. 24 hr food and water intake was measured between day 2-3 and between day 6-7. With two animals per cage, food intake and water intake per animal in a cage was assessed by dividing the food intake and water intake of a cage by two.

Experimenters were blinded to the treatment allocation of animals during termination, blood sampling and sample analyses.

The blood and urine concentrations of zibotentan and dapagliflozin were determined by a bioanalytical method using liquid chromatography with mass spectrometric detection (LC-MS/MS).

Whole blood samples for bioanalysis of dapagliflozin and zibotentan followed the same procedure. A volume of 20 μL whole blood was precipitated with 150 μL acetonitrile containing internal standard and quickly vortexed, followed by a 20 min centrifugation at 3220 g and 4° C. The supernatant was transferred to a fresh deep well plate and diluted 1:1 with water prior to LC-MS analysis. Matrix matched calibration samples and blanks were treated in the same way as study samples. Zibotentan samples were further diluted twice and three times at a 1:10 ratio with 33% acetonitrile, to ensure all diluted samples were detectable within the calibration range.

Sample concentrations were determined against matrix-spiked calibration standards over a range of 0.010 μM-10.0 μM for dapagliflozin and 0.75 μM-376PM for zibotentan, applying weighted linear regression ($1/X^2$) using Waters TargetLynx software version XS V4.2 SCN986. The calibration sample residuals showed homoscedastic distribution. Analytical bias was <15% over the concentration range for both analytes.

Samples were analyzed by using reversed-phase high-pressure liquid chromatography with rapid gradient elution. Compounds were detected with Waters Xevo TQ-S triple quadrupole mass spectrometer (Waters Corporation, Milford, MA, USA). The chromatographic separation was performed by an ACQUITY BEH C18 1.8 μM, 2.1×50 mm column at a temperature of 40° C. Mobile phase A was 2% acetonitrile and 0.2% formic acid in water (A), and mobile phase B was 0.2% formic acid in acetonitrile (B). Separation was achieved using the following elution gradient: 0 min to 1.5 min, 4% B ramping up to 95% B; 1.5 min to 2.3 min, kept at 95% B; 2.3 min to 2.4 min, 95% B to 4% B and kept at 4% B until 2.7 min. The flow rate was 0.7 mL/min. Zibotentan eluted after 0.82 min and was detected in positive electrospray mode using multiple reaction monitoring of transition (425.3 m/z>139.25 m/z).

Samples were analyzed by reversed-phase high-pressure liquid chromatography with rapid gradient elution. Compounds were detected with Waters Xevo TQ-S triple quadrupole mass spectrometer (Waters Corporation, Milford, MA, USA). Mobile phase A was 1M ammonium acetate/acetonitrile/water (0.1/2/97.5, v/v/v), and mobile phase B was 1M ammonium acetate/acetonitrile (0.1/99.5, v/v). Separation was performed by an ACQUITY BEH C18 1.8 μM, 2.1×50 mm column from Waters using the following gradient: 0 min to 2.5 min, 4% B ramping to 60% B; 2.5 min to 2.9 min, 60% B to 95% B; 2.9 min to 3.4 min kept at 95% B, and from 3.4 to 3.5 min mobile phase B was returned to 4% B and kept at 4% B until 4 min. The flow rate was 0.6 mL/min and column temperature was 40° C. Dapagliflozin eluted after 2.19 min and was detected in negative electrospray mode with transitions 407.1>329.07 for dapagliflozin, and 413.0>335.13 for the $^{13}C_6$-dapagliflozin internal standard.

Bioanalysis of zibotentan in rat urine: 50 μL of PBS containing 5% BSA was added to 50 μL of urine sample followed by addition of 500 μL acetonitrile containing nifedipine as internal standard. Samples were vortexed for 1 min and centrifuged at 2400 g for 5 min at 4° C. 400 μL of the supernatant was transferred to a new plate and dried down under heated nitrogen. Samples were reconstituted in 100 μL deionised water/formic acid (100/0.2, v/v), vortex mixed, and centrifuged prior to analysis. Matrix matched calibration samples, quality control samples, and blanks were treated in the same way as study samples. Samples were analyzed on an Acquity i-class UPLC system (Waters, Milford, MA, USA) coupled to an API 4500 (Sciex LLC, Framingham, MA, USA). Mobile phase A was acetonitrile with 0.2% formic acid and mobile phase B was water with 0.2% formic acid. Separation was done over an Acquity UPLC BEH C18 column (50 mm×2.1 mm, 1.7 um particle size from Waters) using the following gradient: 0 min to 1.5 min, 5% A to 100% A; 1.5 min to 2.0 min, 100% A to 100% A; 2.0 min to 2.5 min, 100% A to 5% A. The flow rate was 0.75 mL/min and column temperature was 60° C. Zibotentan (425.1 m/z>361.2 m/z) was analyzed in positive ionization mode with a source temperature of 700° C., and ion spray voltage of 5000 V.

The lower limit of quantification (LLOQ) was 0.010 µM, analytical bias was <15%, except for the lowest QC-standard where CV % was 13.6% and bias 21.0%.

Bioanalysis of dapagliflozin in rat urine: 50 µL of PBS containing 5% BSA was added to 50 µL of urine sample followed by addition of 500 µL acetonitrile/formic acid (100/0.5, v/v) containing nifedipine as internal standard. Samples were vortexed for 1 min and centrifuged at 2400 g for 5 min at 4° C. 450 µL of the supernatant was transferred to a new plate and dried down under heated nitrogen. Samples were reconstituted in 400 µL 1M ammonium acetate/water/formic acid (20/75/5, v/v/v) and vortex mixed. Samples were further purified by solid phase extraction (SPE) using a SOLA HRP (10 mg) SPE plate (ThermoFisher Scientific, Waltham, MA, USA) on a liquid handling robot. The plate was conditioned with 450 µL of methanol followed by 450 µL of 1M ammonium acetate/water/formic acid (20/75/5, v/v/v). Samples were loaded onto the SPE plate and washed with 450 µL of 1M ammonium acetate/water/formic acid (20/75/5, v/v/v) and with 450 µL of acetonitrile/water (95/5, v/v). Samples were eluted twice with 250 µL of acetonitrile/deionised water/acetic acid (80/20/1, v/v/v) and dried under a stream of heated nitrogen. Samples were reconstituted in 100 µL deionised, vortex mixed, and centrifuged prior to analysis. Matrix matched calibration samples quality control samples and blanks were treated in the same way as study samples.

Samples were analyzed on an Acquity i-class UPLC system (Waters, Milford, MA, USA) coupled to an API 4500 (Sciex LLC, Framingham, MA, USA). Mobile phase A was 1M ammonium acetate/acetonitrile/water (0.5/95/4.5, v/v/v), and mobile phase B was 1M ammonium acetate/acetonitrile/water (0.5/25/74.5, v/v/v). Separation was done over an Acquity UPLC HSS T3 column (50 mm×2.1 mm, 1.8 µm particle size from Waters) using the following gradient: 0 min to 3.0 min, 5% A to 50% A; 3.0 min to 3.5 min, 50% A to 100% A; 3.5 min to 4 min, 100% A to 5% A. The flow rate was 0.45 mL/min and column temperature was 25° C. The acetate adduct of dapagliflozin (467.2 m/z>329.0 m/z) was used for quantitation and it was analyzed in negative ionization mode with a source temperature of 750° C., and ion spray voltage of −4500 V. The LLOQ was 0.010 µM, CV and bias were generally <5%, (at the lowest QC-standard, 0.03 µM, CV was 10.3%).

Plasma and Urine Albumin, Creatinine, Glucose, Urea, Potassium and Sodium levels were analyzed using an ABX Pentra 400 instrument (Horiba Medical, Irvine, California, USA) according to the manufacturers protocol.

For Hct and Hb analysis, 100 µl of blood from rat's tail vein was collected and measured using CG8 cartridges analysed with an iSTAT instrument (Abbott Point of Care Inc, Abbot Park, IL, USA).

The data for each feature measured was checked for a normal distribution and where appropriate a log transformation was applied to data with a non-normal distribution using R. Since the data were grouped by one factor Zibotentin doses or combined therapy, a one-way ANOVA was used to analyse traits measured at a single time point (GraphPad version 8 or R statistics package emmeans) and a linear mixed effects model (nlme package) in R was used to analyse multiple measures data for body weight. The differences between groups were tested using either a Dunnett test (emmeans package in R or GraphPad v8) when comparing treated groups to the vehicle group or a Tukey comparison (emmeans package in R or Graphpad v8.) for specific pairwise comparisons of treated groups. All model assumptions were checked using the model diagnostic plots in R statistics. Results are expressed as the Mean±standard error of the Mean (SEM) for pharmacodynamic parameters and Mean±standard deviation (SD) for compound concentration in blood and urine. Significance was set at p<0.05.

Results

Figure 2:
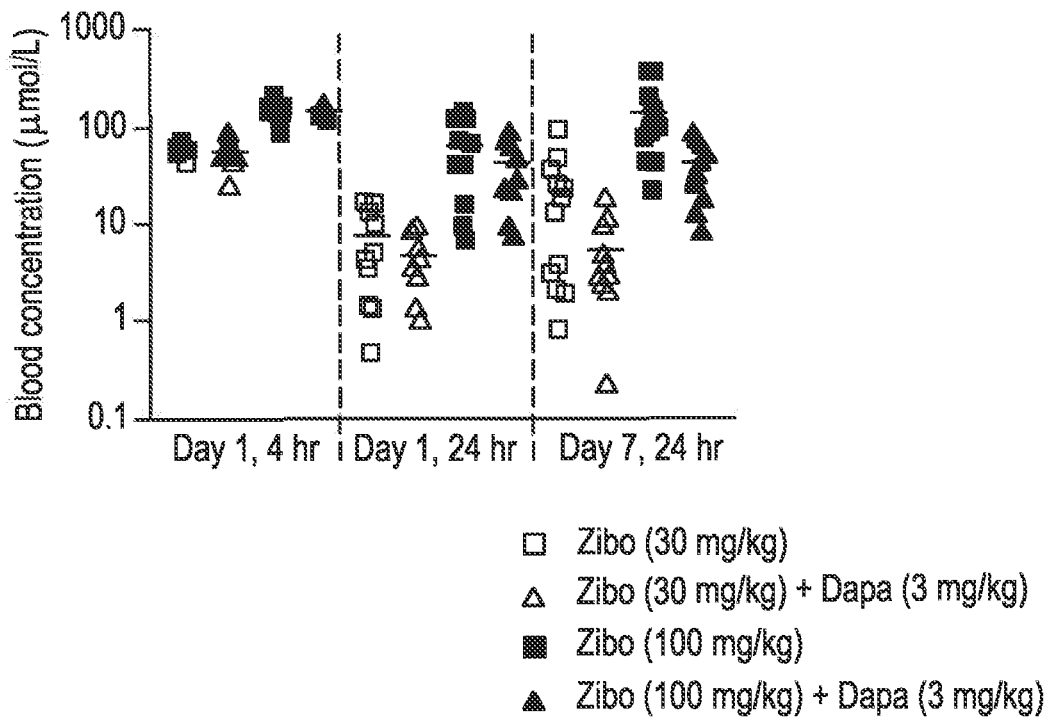
FIG. 2 shows the individual zibotentan blood concentrations in Example 1, Experiment 2 following oral administration of zibotentan alone or in combination with dapagliflozin.

Concentrations of zibotentan above the LLOQ were measured in all blood samples collected 4 hr or 24 hr after first dose or 24 hr after last dose from animals that received zibotentan, confirming exposure to zibotentan (Table 1 and Table 2, FIG. 1 and FIG. 2).

TABLE 1

Zibotentan (Zibo) blood concentrations (µmol/L) in Experiment 1

|  | Vehicle | Zibo (30 mg/kg) | Zibo (100 mg/kg) | Zibo (300 mg/kg) |
|---|---|---|---|---|
| 4 hr post first dose | <LLOQ (10) | 53.8 ± 17.40 (10) | 134 ± 43.8 (10) | 247 ± 46.0 (10) |
| 24 hr post first dose | <LLOQ (10) | 4.68 ± 3.93 (10) | 39.1 ± 38.1 (10) | 176 ± 108 (10) |
| 24 hr post last dose | 0.272 ± 0.146 (6) | 7.39 ± 10.38 (9) | 39.0 ± 32.4 (10) | 249 ± 193 (10) |

Data presented are Mean ± SD (number of samples).
LLOQ Lower limit of quantification
SD Standard deviation

TABLE 2

Zibotentan (Zibo) and dapagliflozin (Dapa) blood concentrations in Experiment 2

|  | Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|---|
| Dapagliflozin (µmol/L) | | | | | | |
| 4 hr post first dose | — | — | — | 1.94 ± 0.517 (11) | 1.90 ± 0.309 (12) | 2.07 ± 0.292 (11) |
| 24 hr post first dose | — | — | — | 0.086 ± 0.052 (11) | 0.133 ± 0.043 (11) | 0.212 ± 0.0649 (12) |
| 24 hr post last dose | — | — | — | 0.048 ± 0.019 (12) | 0.111 ± 0.042 (12) | 0.172 ± 0.050 (12) |
| Zibotentan (µmol/L) | | | | | | |
| 4 hr post first dose | — | 61.1 ± 8.67 (12) | 161 ± 31.0 (10) | — | 59.9 ± 19.1 (12) | 150 ± 18.8 (11) |

TABLE 2-continued

Zibotentan (Zibo) and dapagliflozin (Dapa) blood concentrations in Experiment 2

|  | Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|---|
| 24 hr post first dose | — | 7.80 ± 6.19 (12) | 63.9 ± 46.9 (12) | — | 4.59 ± 2.69 (11) | 44.3 ± 28.8 (12) |
| 24 hr post last dose | — | 22.9 ± 27.2 (12) | 136 ± 123 (12) | — | 5.40 ± 5.29 (12) | 42.4 ± 26.7 (12) |

Data presented are Mean ± SD (number of samples).
LLOQ Lower limit of quantification
SD Standard deviation
— Not detected, all concentrations below LLOQ.

Figure 3:
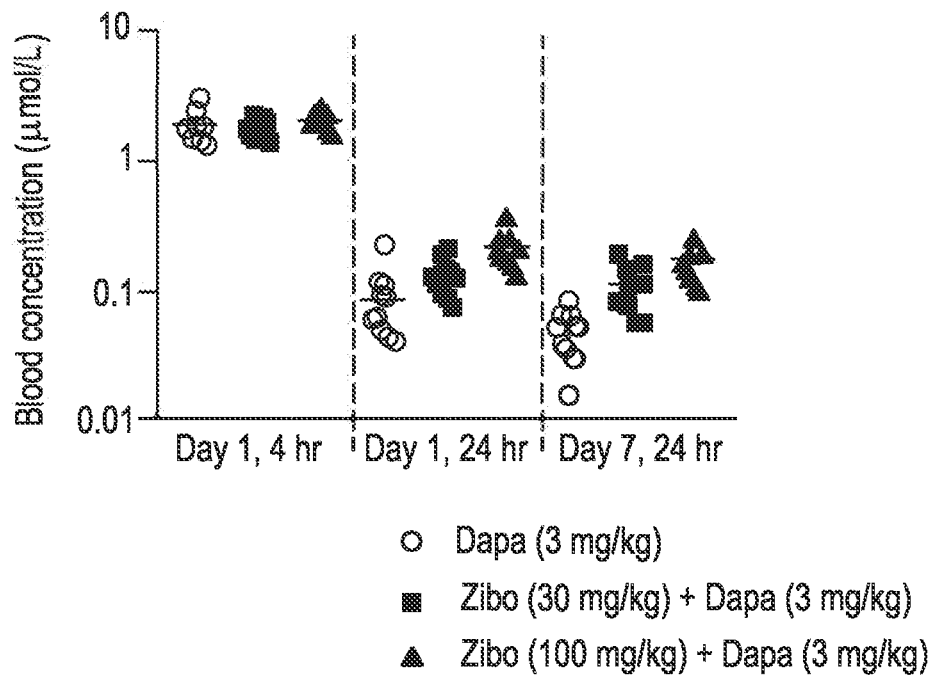
FIG. 3 shows individual dapagliflozin blood concentrations in Example 1, Experiment 2 following oral administration of dapagliflozin alone or in combination with zibotentan.

Concentrations of dapagliflozin above the LLOQ were measured in all blood samples collected 4 hr or 24 hr after first dose or 24 hr after last dose from animals that received dapagliflozin, confirming exposure to dapagliflozin (FIG. 3, Table 2). In Experiment 2, concentrations of zibotentan above the LLOQ were measured in all urine samples collected overnight between days 3 and 4 from animals that received zibotentan (Table 3) and concentrations of dapagliflozin above the LLOQ were measured in all urine samples from animals that received dapagliflozin (Table 3).

TABLE 3

Amount of dapagliflozin (Dapa) and zibotentan (Zibo) excreted in urine in Experiment 2

| Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|
| Dapagliflozin (µmol) | | | | | |
| — | — | — | 0.198 ± 0.0637 (12) | 0.293 ± 0.0600 (11) | 0.343 ± 0.107 (12) |
| Zibotentan (µmol) | | | | | |
| 0.00127 ± 0.00180 (5) | 2.17 ± 1.88 (12) | 3.21 ± 1.20 (11) | — | 1.11 ± 0.531 (11) | 5.24 ± 2.93 (12) |

Data presented are Mean ± SD (number of samples).
LLOQ Lower limit of quantification
SD Standard deviation
— Not detected, all concentrations below LLOQ In Experiment 1, quantifiable concentrations of zibotentan were detected in 6 of the blood samples from control animals on day 14. The apparent concentrations of zibotentan in these positive samples were at least 13-fold lower (using the highest observed (0.54 µM) vehicle animal in relation to mean (7.39 µM) in 30 mg/kg group) than the mean blood concentration in the low dose group (30 mg/kg). In Experiment 2, there were no concentrations of zibotentan or dapagliflozin above LLOQ in blood samples from control animals, but concentrations of zibotentan above LLOQ were detected in 5 of the urine samples from control animals. The amount of zibotentan excreted in urine in these samples were at least 190-fold lower than the mean amount excreted in the zibotentan-treated group showing lowest amount in urine (30 mg/kg zibotentan+3 mg/kg dapagliflozin).

In Experiment 2, the zibotentan blood concentrations at 24 hr after last dose were 3- to 4-fold lower in the groups where zibotentan were combined with dapagliflozin compared to the groups receiving zibotentan alone.

Figure 4:
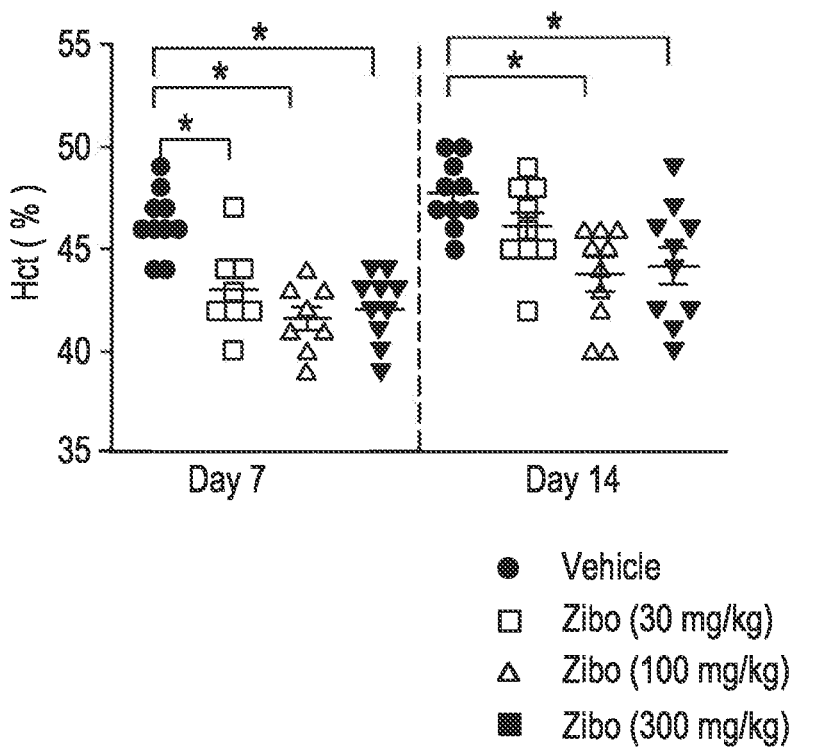
FIG. 4 shows the effect of zibotentan on Hct concentration in Example 1, Experiment 1.

Zibotentan caused a significant ($p<0.05$) decrease in Hct concentration compared to vehicle at all doses (30 mg/kg, 100 mg/kg and 300 mg/kg) on day 7 and for 100 mg/kg and 300 mg/kg on day 14 (FIG. 4).

Figure 5:
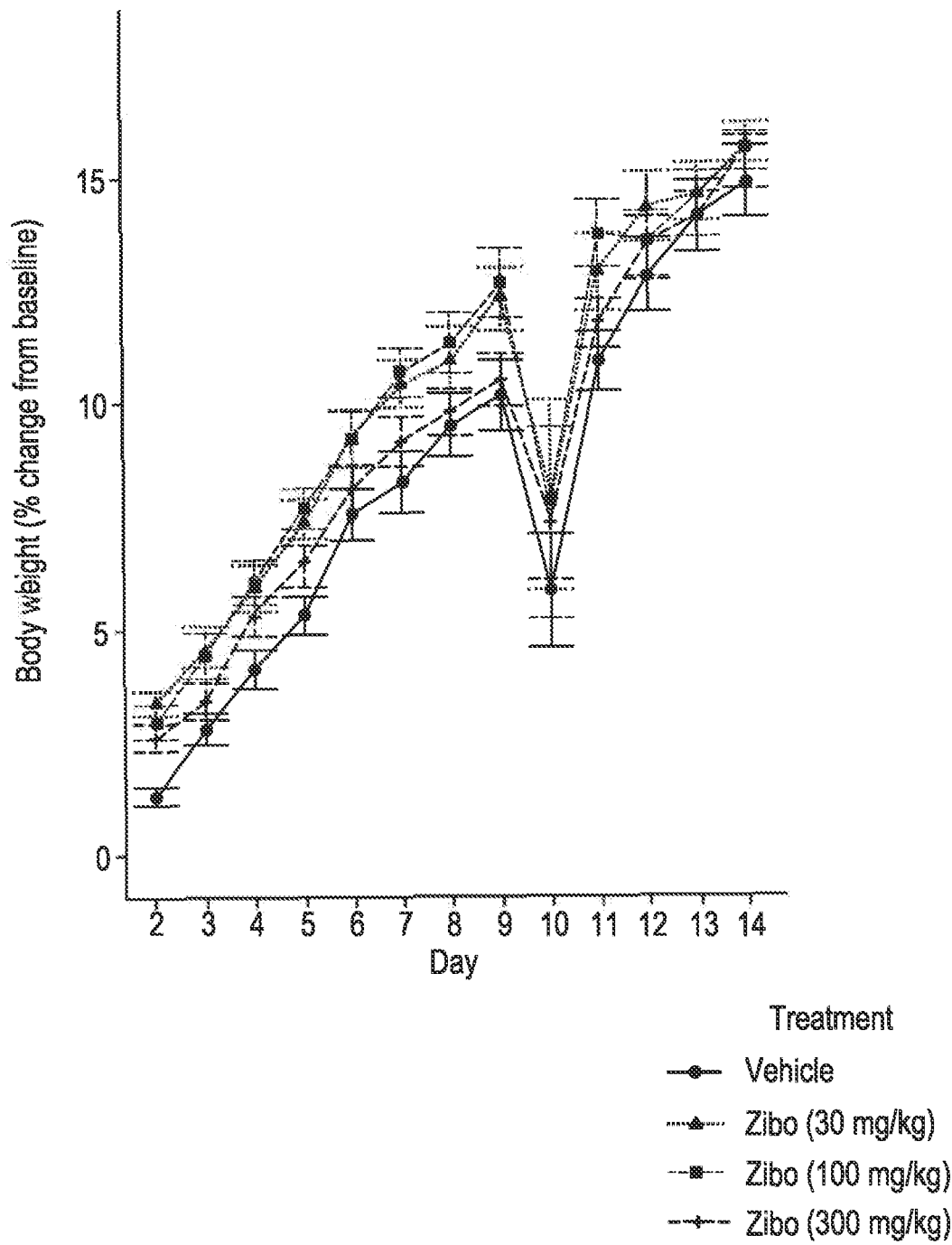
FIG. 5 shows the effect of zibotentan on body weight in Example 1, Experiment 1.

Body weight was measured daily for each dose of zibotentan (30, 100 and 300 mg/kg) and compared to vehicle. There was no difference in body weight change for any of the zibotentan treated groups compared to vehicle (Table 4, FIG. 5). On day 10 the animals body weight decreased due to being placed in metabolic cages.

TABLE 4

Comparison of body weight between zibotentan (30, 100 and 300 mg/kg) and vehicle

| Treated | Control | Difference* | Std error | p.value |
|---|---|---|---|---|
| Zibo 30 mg/kg | Vehicle | 0.02 | 0.01 | 0.14 |
| Zibo 100 mg/kg | Vehicle | 0.02 | 0.01 | 0.12 |
| Zibo 300 mg/kg | Vehicle | 0.01 | 0.01 | 0.73 |

*Differences in means are expressed on the log scale and were estimated from a linear mixed effects model and a Dunnett post hoc test.

Zibotentan caused a significant decrease in Hb compared to vehicle at all three doses (30, 100 and 300 mg/kg) on day 7 and for the two higher doses (100 and 300 mg/kg) on day 14 (Table 5).

TABLE 5

Effect of zibotentan (Zibo) on Hb in Experiment 1

| Parameters | Vehicle | Zibo (30 mg/kg) | Zibo (100 mg/kg) | Zibo (300 mg/kg) |
|---|---|---|---|---|
| Day 7 Hb (g/L) | 157.4 ± 1.68 | 146.4 ± 2.51* | 141.5 ± 2.02* | 143.2 ± 1.79* |
| Day 14 Hb (g/L) | 162.2 ± 1.77 | 156.8 ± 2.43 | 148.5 ± 2.49* | 150.3 ± 3.13* |

Effect of 30, 100 and 300 mg/kg of zibotentan on Hb.
N = 8-10/group,
*$p < 0.05$ vs vehicle.
Data analysis used one-way ANOVA, and Dunnett's test for multiple comparisons, Data presented as Mean ± SEM.

There was no change in the level of Na, K, glucose and urea in the plasma in response to different doses of zibotentan compared to vehicle as shown in Table 6.

TABLE 6

Effect of zibotentan (Zibo) on plasma Na, K, glucose and urea in Experiment 1

| Parameters | Vehicle | Zibo (30 mg/kg) | Zibo (100 mg/kg) | Zibo (300 mg/kg) |
|---|---|---|---|---|
| Na (mmol/L) | 136.4 ± 0.70 | 137.0 ± 0.96 | 137.2 ± 0.97 | 139.4 ± 0.86 |
| K (mmol/L) | 4.35 ± 0.11 | 4.50 ± 0.06 | 4.52 ± 0.06 | 4.76 ± 0.09 |
| Glucose (mmol/L) | 9.23 ± 0.29 | 9.76 ± 0.28 | 9.65 ± 0.30 | 9.34 ± 0.13 |
| Urea (mmol/L) | 4.60 ± 0.25 | 4.64 ± 0.20 | 4.77 ± 0.25 | 4.94 ± 0.39 |

Effect of different doses of zibotentan on plasma Na, K, glucose and urea.
N = 8-10/group.
Data analysis used one-way ANOVA, and Dunnett's test for multiple comparisons.
Data presented as Mean ± SEM.

There was no change in the level of urinary volume, Na, K, urea, creatinine and glucose in response to different doses of zibotentan compared to vehicle as shown in Table 7.

TABLE 7

Effect of zibotentan (Zibo) on urinary volume and Na, K, urea, creatinine, glucose in the urine in Experiment 1

| Parameters | Vehicle | Zibo (30 mg/kg) | Zibo (100 mg/kg) | Zibo (300 mg/kg) |
|---|---|---|---|---|
| Urine volume (ml) | 24.79 ± 2.85 | 28.19 ± 2.99 | 23.88 ± 2.02 | 29.09 ± 2.74 |
| Na (mmol) | 13.42 ± 1.27 | 14.05 ± 0.95 | 13.01 ± 1.07 | 13.76 ± 0.76 |
| K (mmol) | 1.62 ± 0.07 | 1.57 ± 0.05 | 1.52 ± 0.06 | 1.44 ± 0.03 |
| Urea (mmol) | 4.73 ± 0.42 | 6.19 ± 1.71 | 4.04 ± 0.39 | 4.60 ± 0.19 |
| Creatine (μmol) | 86.84 ± 3.13 | 88.8 ± 3.3 | 82.8 ± 2.5 | 82.9 ± 3.3 |
| Glucose (mmol) | 0.05 ± 0.0 | 0.01 ± 0.0 | 0.02 ± 0.0 | 0.18 ± 0.1 |

Effect of different doses of zibotentan on urine volume, Na, K, glucose, creatinine and urea.
N = 8-10/group.
Data analysis used one-way ANOVA, and Dunnett's test for multiple comparisons.
Data presented as Mean ± SEM.

Following 14 days of zibotentan treatment, there was an increase in kidney weight with or without normalizing with tibia length for the 300 mg/kg dose compared to vehicle and increase in heart weight for 100 mg/kg zibotentan but this increase was not statistically significant after normalizing with tibia length (Table 8).

TABLE 8

Effect of zibotentan (Zibo) on kidney and heart weight in Experiment 1

| Parameters | Vehicle | Zibo (30 mg/kg) | Zibo (100 mg/kg) | Zibo (300 mg/kg) |
|---|---|---|---|---|
| Kidney (g) | 2.06 ± 0.03 | 2.13 ± 0.04 | 2.16 ± 0.05 | 2.25 ± 2.74* |
| Heart (g) | 1.00 ± 0.01 | 1.00 ± 0.02 | 1.05 ± 0.01* | 0.98 ± 0.00 |
| Tibia length (mm) | 39.35 ± 0.23 | 39.26 ± 0.26 | 39.00 ± 0.13 | 39.09 ± 0.21 |
| Kidney/tibia length (mg/mm) | 52.0 ± 0.89 | 54.00 ± 0.80 | 55.0 ± 1.65 | 57.0 ± 1.39* |
| Heart/tibia length (mg/mm) | 25.00 ± 0.44 | 25.00 ± 0.47 | 27.00 ± 0.37 | 25.00 ± 0.24 |

Effect of 30, 100 and 300 mg/kg of zibotentan on kidney and heart weight.
N = 8-10/group.
Data analysis used one-way ANOVA, and Dunnett's test for multiple comparisons.
Data presented as Mean ± SEM,
*p < 0.05 vs vehicle.

The Hct data were analysed using a linear mixed effects model to estimate the marginal means and standard deviations within the vehicle and treated groups estimated at day 3, day 7 and overall for the entire study for post hoc comparisons. Treatment groups were compared to the vehicle to determine whether there were effects on Hct compared to the vehicle treated control group (Dunnett test), and the zibotentan treated groups were compared to zibotentan plus dapafliglozin groups (using a Tukey test) to determine if the combined therapy mitigated the effect of zibotentan on Hct.

Figure 6B:
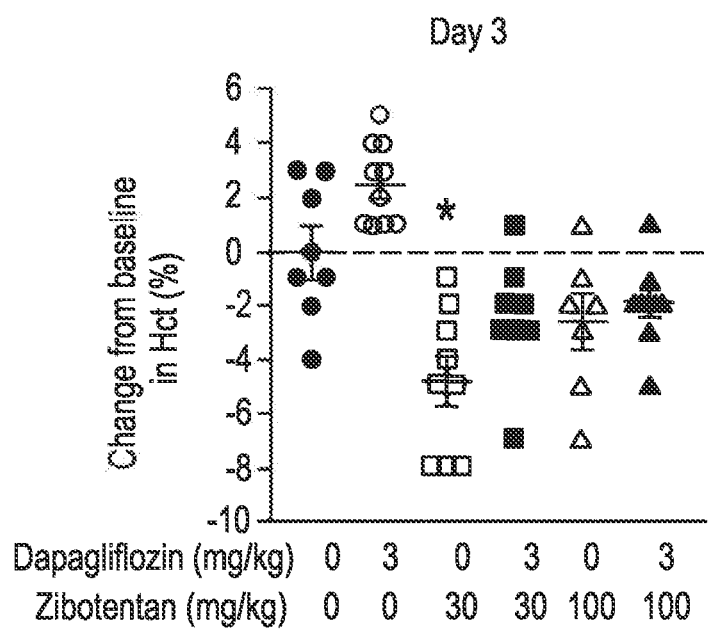
Figure 6C:
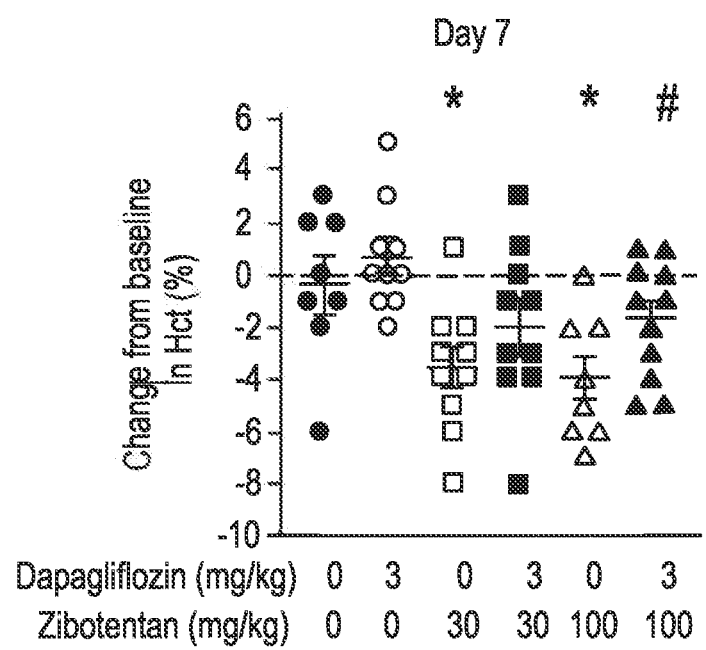

There was no difference on the level of absolute Hct value at baseline across groups (FIG. 6A). On day 3, zibotentan (30 mg/kg and 100 mg/kg) administered with or without dapagliflozin (3 mg/kg), decreased Hct compared to vehicle (FIG. 6B, Table 9A). On day 7, zibotentan (30 mg/kg and 100 mg/kg) decreased Hct compared to vehicle and both doses, when co-administered with dapagliflozin (3 mg/kg), resulted in a Hct that was similar to vehicle (FIG. 6C, Table 9B). Overall, zibotentan 100 mg/kg plus dapagliflozin had higher Hct levels than zibotentan 100 mg/kg alone (Table 9C).

TABLE 9A

Comparison of Hct levels by treatment groups pairwise
and to a common control on day 3 of treatment

| Group 1 | Group 2 | estimate | std. error | p.value |
|---|---|---|---|---|
| Dapa (3.0 mg/kg) | Vehicle | 0.03 | 0.02 | 0.42 |
| Zibo (100 mg/kg) + Dapa (3.0 mg/kg) | Vehicle | −0.05 | 0.02 | 0.02 |
| Zibo (100 mg/kg) | Vehicle | −0.08 | 0.02 | 0.0009 |
| Zibo (30 mg/kg) + Dapa (3.0 mg/kg) | Vehicle | −0.06 | 0.02 | 0.01 |
| Zibo (30 mg/kg) | Vehicle | −0.10 | 0.02 | 0.0001 |
| Zibo (100 mg/kg) + Dapa (3.0 mg/kg) | Zibo (100 mg/kg) | 0.03 | 0.02 | 0.08 |
| Zibo (30 mg/kg) + Dapa (3.0 mg/kg) | Zibo (30 mg/kg) | 0.04 | 0.02 | 0.05 |

*Differences in means are expressed on the log scale and were estimated from a linear mixed effects model and a Dunnett post hoc test for comparison with vehicle and Tukey comparisons for pairwise comparisons.

On day 7, zibotentan mono treatment at 30 mg/kg and 100 mg/kg induced decrease in Hct, but this effect was lost when zibotentan was combined with dapagliflozin (FIG. 6C, Table 9B).

TABLE 9B

Comparison of Hct levels by treatment groups pairwise
and to a common control on day 7 of treatment

| Group 1 | Group 2 | Difference* | Std Error | p.value |
|---|---|---|---|---|
| Dapa (3.0 mg/kg) | Vehicle | 0.01 | 0.02 | 0.92 |
| Zibo (100 mg/kg) + Dapa (3 mg/kg) | Vehicle | −0.03 | 0.02 | 0.52 |
| Zibo (100 mg/kg) | Vehicle | −0.08 | 0.02 | 0.0003 |
| Zibo (30 mg/kg) + Dapa (3 mg/kg) | Vehicle | −0.05 | 0.02 | 0.12 |
| Zibo (30 mg/kg) | Vehicle | −0.06 | 0.02 | 0.02 |
| Zibo (100 mg/kg) + Dapa (3 mg/kg) | Zibo (100 mg/kg) | 0.06 | 0.02 | 0.009 |
| Zibo (30 mg/kg) + Dapa (3 mg/kg) | Zibo (30 mg/kg) | 0.01 | 0.02 | 0.93 |

TABLE 9C

Difference in Hct means by treatment group
compared to vehicle for all time points

| Group 1 | Group 2 | Difference | Std Error | pvalue |
|---|---|---|---|---|
| Dapa (3 mg/kg) | Vehicle | 0.01 | 0.012 | 0.85 |
| Zibo (100 mg/kg) + Dapa (3 mg/kg) | Vehicle | −0.03 | 0.012 | 0.10 |
| Zibo (100 mg/kg) | Vehicle | −0.06 | 0.012 | <0.0001 |
| Zibo (30 mg/kg) + Dapa (3 mg/kg) | Vehicle | −0.04 | 0.012 | 0.01 |
| Zibo (30 mg/kg) | Vehicle | −0.05 | 0.012 | 0.0003 |
| Zibo (100 mg/kg) + Dapa (3 mg/kg) | Zibo (100 mg/kg) | −0.03 | 0.012 | 0.01 |
| Zibo (30 mg/kg) + Dapa (3 mg/kg) | Zibo (30 mg/kg) | −0.01 | 0.012 | 0.46 |

Figure 7:
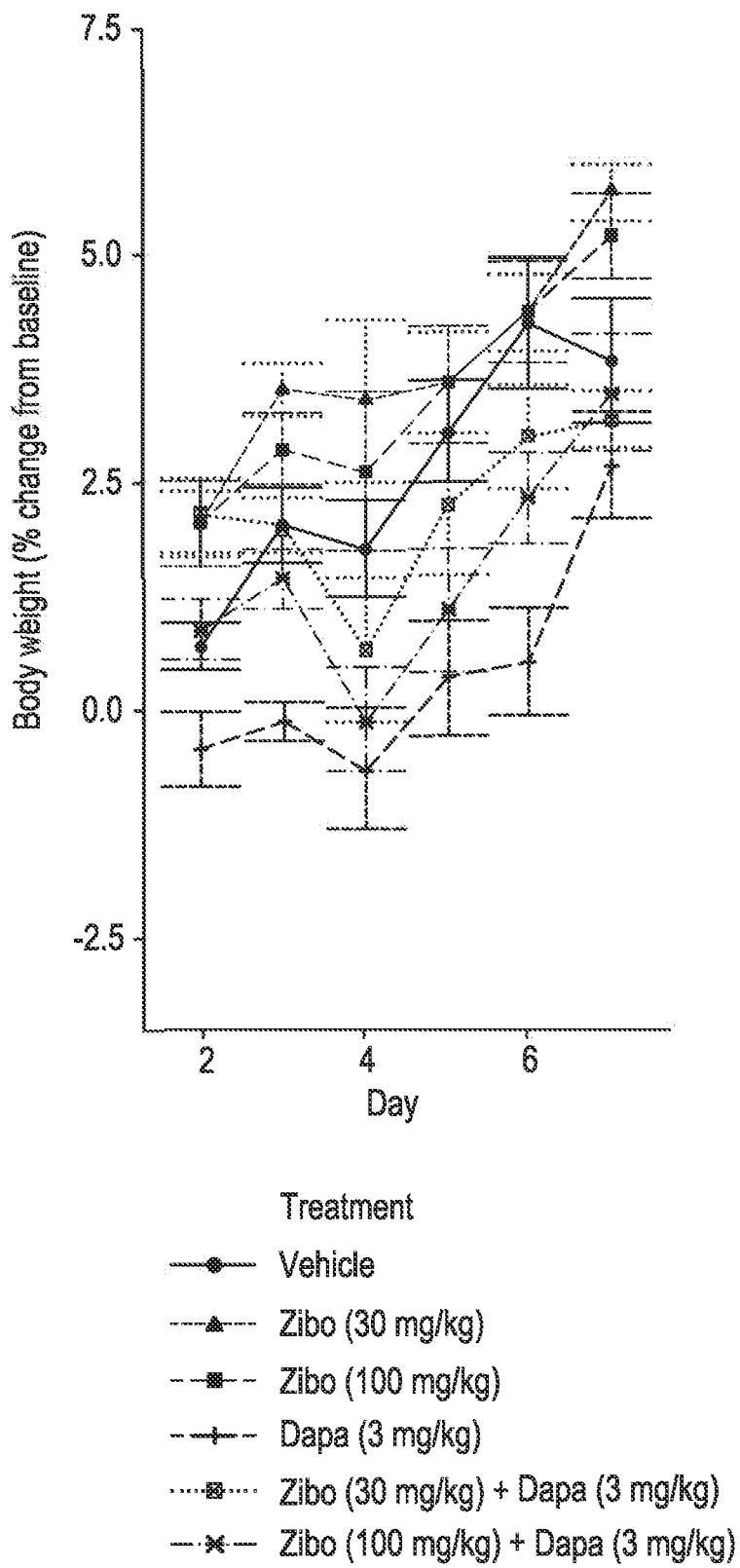
FIG. 7 shows the effect of zibotentan, dapagliflozin and the combination on body weight in Example 1, Experiment 2.

Dapagliflozin is known to increase weight loss (Hansen et al., *Endocr Pract.* 2014; 20(11): 1187-1197). To assess the effect of the combined therapy on weight loss, body weight was measured every day and was compared using a linear mixed effects model. Vehicle treated animals gained weight during the administration period, as expected, dapagliflozin monotreatment prevented this BW gain compared to vehicle (p<0.05), while zibotentan alone or in combination with dapagliflozin did not (FIG. 7, Table 10).

TABLE 10

Group comparisons for changes in body weight
over the entire study by treatment group

| Group 1 | Group 2 | Difference | Std Error | P value |
|---|---|---|---|---|
| Zibo (30 mg/kg) | Vehicle | 0.01 | 0.01 | 0.06 |
| Zibo (100 mg/kg) | Vehicle | 0.01 | 0.01 | 0.11 |
| Dapa (3 mg/kg) | Vehicle | −0.03 | 0.01 | <0.001 |
| Zibo (30 mg/kg) + Dapa (3 mg/kg) | Vehicle | 0.00 | 0.01 | >0.99 |
| Zibo (100 mg/kg) + Dapa (3 mg/kg) | Vehicle | −0.01 | 0.01 | 0.14 |
| Zibo (100 mg/kg) + Dapa (3 mg/kg) | Zibo (100 mg/kg) | 0.04 | 0.01 | 0.001 |
| Zibo (30 mg/kg) + Dapa (3 mg/kg) | Zibo (30 mg/kg) | 0.01 | 0.01 | 0.07 |

Vehicle treated animals gained weight during the administration period, as expected, dapagliflozin monotreatment prevented this BW gain compared to vehicle (p < 0.05), while zibotentan alone or in combination with dapagliflozin did not (FIG. 7).

Figure 8A:
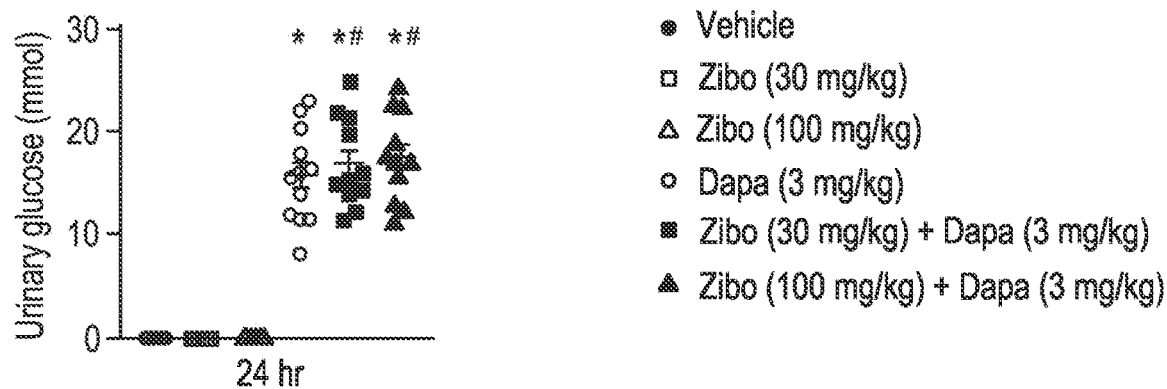
FIGS. 8A-8C show the effects of dapagliflozin and zibotentan on glucosuria (FIG. 8A), water (FIG. 8B), and food intake (FIG. 8C) in Example 1, Experiment 2.
Figure 8B:
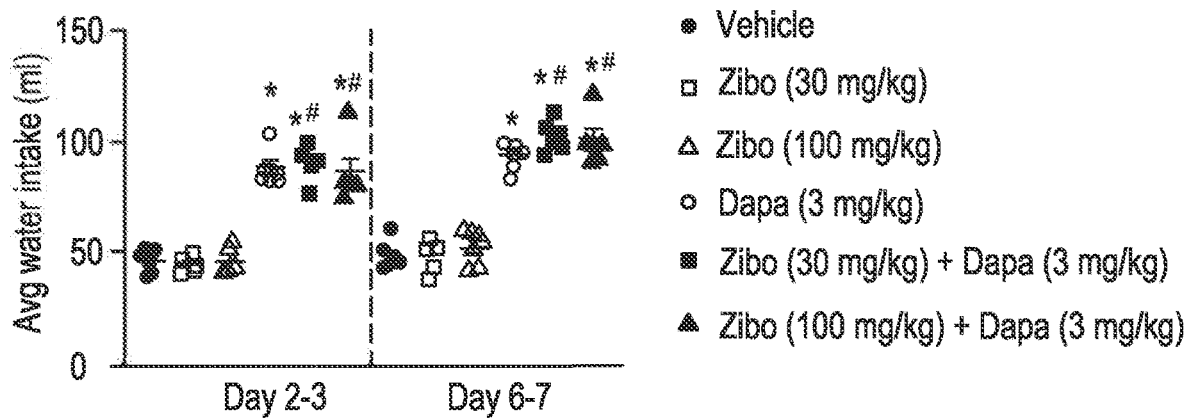
Figure 8C:
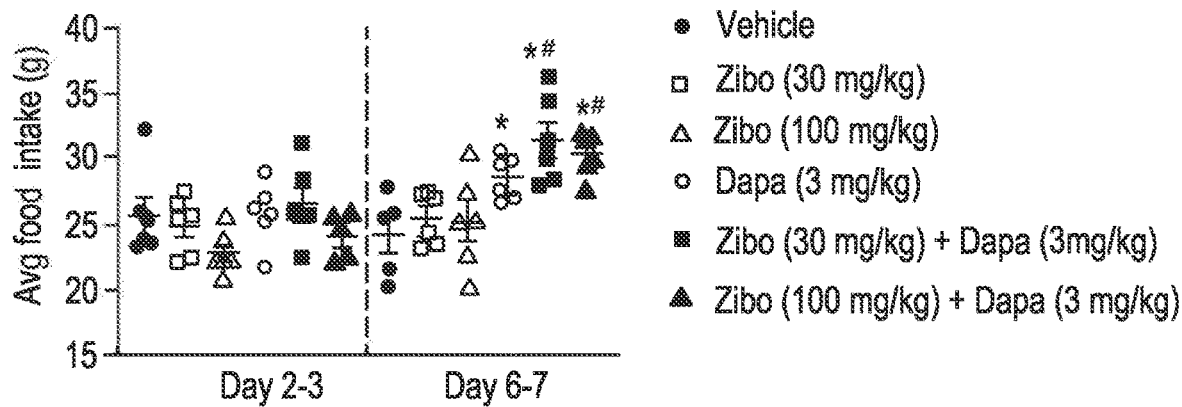

Dapagliflozin significantly increased urine glucose excretion, while there was no effect of zibotentan (FIG. 8A). Co-administration of zibotentan did not alter dapagliflozin mediated increase in urine glucose (FIG. 8A). Water and food intake were unchanged compared to vehicle by zibtentan. Dapagliflozin treatment increased water and food intake compared to vehicle as shown in FIG. 8B and FIG. 8C. Animals co-administered dapagliflozin and zibotentan significantly increased water intake and food intake when compared to vehicle and to a similar level observed in animals administered dapagliflozin alone (FIG. 8B and FIG. 8C respectively).

TABLE 11

Effect of zibotentan (Zibo) and dapagliflozin (Dapa) on Hb in Experiment 2

| Parameters | Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|---|
| Basal Hb (g/L) | 159.4 ± 2.44 | 160.2 ± 1.62 | 158.5 ± 2.00 | 157.9 ± 2.34 | 159.3 ± 2.17 | 158.7 ± 1.04 |
| Day 3 Hb (g/L) | 159.1 ± 2.20 | 144.4 ± 2.32* | 147.5 ± 1.96* | 164.4 ± 1.42* | 151.3 ± 1.62# | 152.4 ± 1.02# |
| Day 7 Hb (g/L) | 157.5 ± 1.91 | 148.6 ± 1.86 | 144.8 ± 1.69* | 159.1 ± 1.88* | 149.7 ± 2.80 | 152.9 ± 1.99# |

Effect of 30 mg/kg and 100 mg/kg zibotentan with or without 3 mg/kg dapagliflozin, 3 mg/kg dapagliflozin alone and vehicle on Hb, N = 8-12/group,
*$p < 0.05$ vs vehicle,
$p < 0.05$ vs zibotentan mono-treated groups.
Data analysis used one-way ANOVA, and Tukey's test for multiple comparisons. Data presented as Mean ± SEM.

Plasma Na, K, glucose, urea concentrations were unaltered by treatment with zibotentan, dapagliflozin or their combination compared to vehicle as shown in Table 12. Zibo (100 mg/kg) monotreatment or in combination with Dapa (3 mg/kg) significantly increase plasma creatinine compared to vehicle ($p<0.05$), shown in Table 12.

TABLE 12

Effect of zibotentan (Zibo), dapagliflozin (Dapa) or their combination on plasma Na, K, glucose, urea and creatinine concentration in Experiment 2

| Parameters | Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|---|
| Na (mmol/L) | 138.9 ± 0.90 | 139.1 ± 1.23 | 138.4 ± 0.76 | 137.6 ± 0.74 | 138.4 ± 0.96 | 139.2 ± 0.87 |
| K (mmol/L) | 3.99 ± 0.68 | 4.17 ± 0.07 | 4.13 ± 0.06 | 3.68 ± 0.10 | 3.96 ± 0.05 | 4.0 ± 0.08 |
| Glucose (mmol/L) | 8.64 ± 0.28 | 8.96 ± 0.19 | 8.73 ± 0.17 | 8.98 ± 0.28 | 8.49 ± 0.39 | 9.41 ± 0.21 |
| Urea (mmol/L) | 4.51 ± 0.30 | 4.47 ± 0.25 | 4.25 ± 0.18 | 4.34 ± 0.14 | 3.95 ± 0.18 | 3.91 ± 0.12 |
| Creatinine (μM) | 15.35 ± 0.75 | 17.58 ± 0.68 | 18.08 ± 0.62* | 14.62 ± 0.44 | 16.64 ± 0.52 | 17.98 ± 0.92* |

Effect of 30 mg/kg and 100 mg/kg zibotentan with or without 3 mg/kg dapagliflozin, 3 mg/kg dapagliflozin alone and vehicle on plasma electrolytes, urea, glucose and creatinine, N = 8-12/group. Data analysis used one-way ANOVA, and Dunnett's test for multiple comparisons. Data presented as Mean ± SEM.

24-hour urine volume and urea excretion were increased in all the dapagliflozin treated groups with or without co-administration of zibotentan. No difference was observed in zibotentan mono-treated groups, compared to vehicle. No change was observed for Na, K and creatinine in any of the treatment groups compared to vehicle as shown in Table 13.

TABLE 13

Effect of zibotentan (Zibo), dapagliflozin (Dapa) and the combination on urinary volume and Na, K, urea and creatinine in the urine in Experiment 2

| Parameters | Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|---|
| Urine volume (ml) | 22.59 ± 2.10 | 19.08 ± 2.98 | 19.08 ± 2.98 | 43.13 ± 5.85* | 48.00 ± 5.71*,# | 53.21 ± 4.82*,# |
| Na (mmol) | 11.58 ± 0.87 | 10.67 ± 0.74 | 10.03 ± 0.95 | 12.60 ± 1.54 | 13.18 ± 1.41 | 14.13 ± 1.19 |
| K (mmol) | 1.26 ± 0.07 | 1.27 ± 0.05 | 1.16 ± 0.06 | 1.40 ± 0.07 | 1.48 ± 0.07 | 1.31 ± 0.07 |

TABLE 13-continued

Effect of zibotentan (Zibo), dapagliflozin (Dapa) and the combination on urinary volume and Na, K, urea and creatinine in the urine in Experiment 2

| Parameters | Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|---|
| Urea (mmol) | 5.07 ± 0.38 | 4.61 ± 0.36 | 4.11 ± 0.34 | 7.43 ± 0.44* | 6.88 ± 0.41*,# | 6.95 ± 0.39*,# |
| Creatinine (μmol) | 70.64 ± 3.02 | 71.33 ± 2.6 | 68.18 ± 3.6 | 76.42 ± 3.5 | 79.09 ± 2.9 | 77.00 ± 3.5 |

Effect of different doses of 30 mg/kg and 100 mg/kg zibotentan with or without 3 mg/kg dapagliflozin, 3 mg/kg dapagliflozin alone and vehicle on urine volume, electrolytes, urea, glucose and creatinine, N = 8-12/group. Data analysis used one-way ANOVA, and Tukey's test for multiple comparisons test. Data presented are Mean ± SEM,
*$p < 0.05$ vs vehicle,
$p < 0.05$ vs zibotentan mono-treated groups.

After seven days of treatment, kidney weight increased in the Zibo 100 mg/kg+Dapa 3 mg/kg group compared to vehicle. Heart weight increased in the Zibo 30 mg/kg group compared to vehicle alone with or without normalizing to tibia length as shown in Table 14.

TABLE 14

Effect of zibotentan (Zibo) and dapagliflozin (Dapa) on kidney and heart weight in Experiment 2

| Parameters | Vehicle | Zibo (30 mg/kg) | Zibo (100 mg/kg) | Dapa (3 mg/kg) | Zibo (30 mg/kg) + Dapa (3 mg/kg) | Zibo (100 mg/kg) + Dapa (3 mg/kg) |
|---|---|---|---|---|---|---|
| Kidney (g) | 1.89 ± 0.04 | 2.05 ± 0.04 | 1.90 ± 0.05 | 2.01 ± 0.05 | 2.07 ± 0.06 | 2.12 ± 0.03* |
| Heart (g) | 0.89 ± 0.01 | 0.96 ± 0.01* | 0.93 ± 0.01 | 0.85 ± 0.02 | 0.91 ± 0.01 | 0.88 ± 0.01 |
| Tibia length (mm) | 39.28 ± 0.19 | 39.28 ± 0.22 | 39.42 ± 0.15 | 38.85 ± 0.23 | 39.88 ± 0.22 | 39.32 ± 0.17 |
| Kidney/tibia length (mg/mm) | 48.33 ± 1.31 | 52.49 ± 1.15 | 48.20 ± 1.35 | 51.96 ± 1.34 | 52.02 ± 1.62 | 53.99 ± 1.13* |
| Heart/tibia length (mg/mm) | 22.82 ± 0.45 | 24.75 ± 0.27* | 23.82 ± 0.46 | 22.08 ± 0.46 | 23.00 ± 0.33 | 23.59 ± 0.36 |

Effect of different doses of 30 mg/kg and 100 mg/kg zibotentan with or without 3 mg/kg dapagliflozin, 3 mg/kg dapagliflozin alone and vehicle on kidney and heart weight. N = 12/group,
*$p < 0.05$ vs vehicle.
Data analysis used one-way ANOVA, and Dunnett's test for multiple comparison. Data presented are Mean ± SEM.

The endothelial receptor A antagonist, zibotentan significantly decreased Hct concentration in 4% salt diet fed male Wistar rats. Co-administration of the SGLT-2 inhibitor dapagliflozin for 7 days significantly reduced zibotentan's effect on Hct concentration. Dapagliflozin attenuates zibotentan-induced fluid retention (haematocrit) reduction in rats.

Example 2

The effect of dapagliflozin on albuminuria was investigated in patients with CKD with and without type 2 diabetes. In this analysis from the Phase 3 DAPA CKD trial, the efficacy of dapagliflozin was assessed to determine whether treatment with dapagliflozin reduces the level of albuminuria in patients with CKD.

In the trial, 4304 patients with estimated glomerular filtration rate 25-75 mL/min/1·73 m$^2$ and urinary UACR 200-5000 mg/g were randomized to dapagliflozin (10 mg) or placebo. Change in albuminuria was assessed as the mean change in log-transformed UACR from baseline to end of study. Regression in UACR stage, defined as a transition from macroalbuminuria (≥300 mg/g) to micro- or normoalbuminuria (<300 mg/g), and progression in UACR stage, defined as a transition from <3000 mg/g to ≥3000 mg/g, were additional endpoints.

Figure 9:
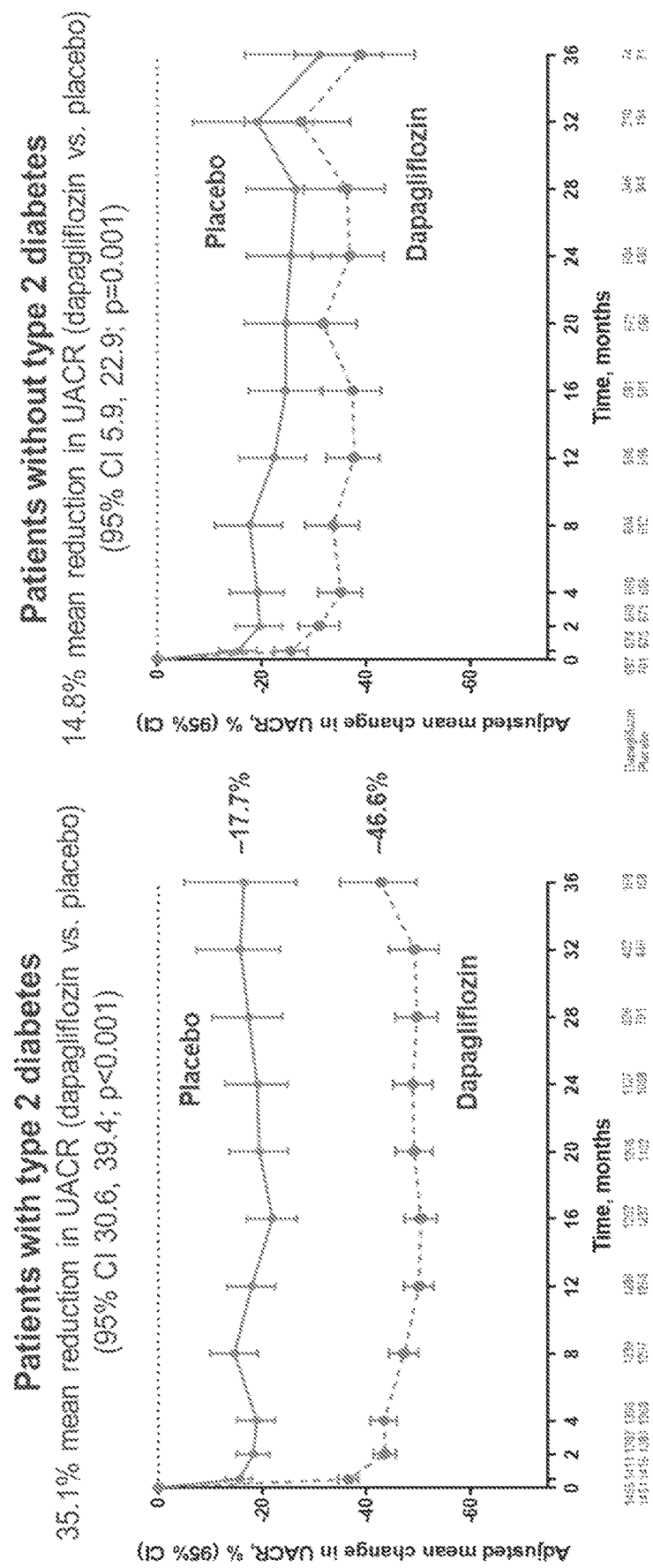
FIG. 9 shows the UACR lowering effect of dapagliflozin in patients with CKD and either Type 2 diabetes or without Type 2 diabetes from the DAPA CKD Phase 3 trial.

In the overall population, the median ($25^{th}$-$75^{th}$ percentile) UACR was 965 (472-1903) mg/g (compared to placebo with a median UACR of 934 (482-1868)). Dapagliflozin, compared to placebo, reduced UACR by 29.3% (95% confidence interval [CI], 25.2-33.1%; $p<0.001$ in patients with and without type 2 diabetes. Stratified by diabetes status, dapagliflozin, compared to placebo, reduced UACR by 35.1% (95% confidence interval [CI], 30.6-39.4%; $p<0.001$) in patients with type 2 diabetes and reduced UACR by 14.8% (95% confidence interval [CI], 5.9-22.9%; $p<0.001$) in patients without type 2 diabetes. Among the 3860 patients with UACR≥300 mg/g at baseline, dapagliflozin increased the likelihood of regression in UACR stage (hazard ratio [HR] 1.81; 95% CI, 1.60-2.05). Among the 3820 patients with UACR<3000 mg/g at baseline, dapagliflozin decreased the risk of progression in UACR stage (HR 0.41; 95% CI, 0.32-0.52). The regression and progression of albuminuria is further stratified by diabetes status and shown as FIG. 9 and FIG. 10. As illustrated by this analysis, treatment with dapagliflozin reduced UACR in patients with CKD regardless of diabetes status.

Example 3

A pre-clinical study of dapagliflozin in combination with zibotentan is ongoing to show mono-agent and combination effects on certain biomarkers indicative of renal and cardiovascular function in male Dahl Salt Sensitive (DSS) rats.

Example 3 will assess the effect of zibotentan alone and the combination of zibotentan and dapagliflozin on body weight, blood pressure (mean arterial pressure—MAP, systolic blood pressure—SBP, and diastolic blood pressure—DBP) and heart rate, urine protein albumin and creatinine, serum creatinine, hematology, echocardiography of the heart and LV diameter and wall thickness, fractional shortening and ejection fraction and kidney (left and right), heart, and lung weight and tibia length in DSS 7-9-week-old rats on 4% salt diet in a 7-week study. Treatment will begin 12 days following the initiation of 4% salt diet.

Formulation for Vehicle: 30% (w/w) PEG400, 2% (w/w) EtOH, 0.5% (w/w) HPMC (10000 cps), 0.1% (w/w) Tween 80, and 67.4% purified water.

Formulation for zibotentan alone: Suspension in 30% (w/w) PEG400, 2% (w/w) EtOH 0.5% (w/w) HPMC 10000 cps 0.1% (w/w) Tween 80 and 67.4% purified water.

Formulation for dapagliflozin in combination with zibotentan: Suspension/Solution in 30% (w/w) PEG400, 2% (w/w) EtOH 0.5% (w/w) HPMC 10000 cps 0.1% (w/w) Tween 80 and 67.4% purified water.

The effect of zibotentan alone and dapagliflozin alone on body weight, blood pressure (MAP, SBP, and DBP) and heart rate, urine protein albumin and creatinine, serum creatinine, hematology, echocardiography of the heart and LV diameter and wall thickness, fractional shortening and ejection fraction and kidney (left and right), heart, and lung weight and tibia length will be determined according to the three groups summarized in Table 15 below:

TABLE 15

Study Groups for Example 3

| Group | Diet | Test Article | Dose (mg/kg) | Nominal Dose Concentration (mg/mL)* | Dose Vol. (mL/kg) | Frequency & Duration | Sample Size |
|---|---|---|---|---|---|---|---|
| A | 4% NaCl Chow | Vehicle | N/A | N/A | 5 | QD, day 12 to study completion | 14 |
| B | 4% NaCl Chow | Zibotentan | 0.75 mg/kg | 0.15 | 5 | | 12 |
| C | 4% NaCl Chow | Dapagliflozin Zibotentan | 3 mg/kg 0.75 mg/kg | 0.6 0.15 | 5 | | 12 |

Whole blood samples (20 μL) from Groups B and C will be collected at weeks 3 and 6 to assess PK. Additional whole blood samples of 200 μL will be collected at week 1 to assess hematology Hct and MCV (via Horiba ABX Micros ESV60). Urine will be collected at weeks 1, 3, and 6 to assess clinical chemistry (via RX Daytona®) to assess serum creatinine and urine protein albumin and creatinine.

Echocardiogram images will be obtained from rats under light anesthesia with 1-2% isoflurane using a VisualSonics Vevo 3100@ Ultrasound Echocardiography System and MX201 15 MHZ microscan transducer. M-Mode (short-axis) images of the left ventricle will be collected for LVEDD, LVESD, AWT, PWT, FS and EF. The left kidney, lungs, and heart will be harvested, decapsulated, and weighed. The tibia will be measured for length and imaged via Xray.

Clinical chemistry and hematology data, Echo data, and body weight and tissue weight (normalized to tibia length) will be analyzed using One-way ANOVA (GraphPad Prism version 7.0a). The statistically significant differences between groups will be tested using the Dunnett test. Blood pressure analysis will be assessed as mean±SEM of MAP, SBP, DBP and heart rate in line-graph form.

Example 4

Clinical trials (ZENITH-CKD) of the dapagliflozin and zibotentan combination are ongoing in a Phase 2b, multi-centre, randomised, double-blind, placebo-controlled, parallel group dose-ranging study to assess the efficacy, safety and tolerability of zibotentan and dapagliflozin in participants with CKD with eGFR between 20 and 60 mL/min/1.73 m2.

Study Design

The study will be conducted in 2 parts, Part A and Part B. In both study parts, participants will be randomised to 12 weeks of treatment plus 2 weeks follow-up. All the variables will be collected to verify the inclusion criteria and additional demographic data such as race/ethnicity, serum creatinine, and height. All analyses (except the interim analyses during Part A) will include data from both parts of the study.

Participants who meet the eligibility criteria will be randomised to the treatments described for Part A or Part B, in addition to receiving background local SoC therapy. To maintain blinding, participants will take both active and placebo study intervention on each dosing day when receiving Zibo/Dapa monotherapy. Participants receiving placebo only will take placebo of both study interventions.

In Part A, 132 eligible participants are planned to be recruited and randomised into 4 treatment arms of 33 participants each:

Zibotentan 5 mg+Dapagliflozin 10 mg once daily.
Zibotentan 5 mg once daily.
Dapagliflozin 10 mg once daily.
Placebo once daily.

An interim analysis of Part A data will be performed when approximately 30 participants in each arm (120 participants) have completed 6 weeks of treatment to assess changes in fluid-related measures (weight gain or BNP). If fluid-related measures meet the specified criteria in at least 5 participants in the zibotentan 5 mg monotherapy arm, this arm will be discontinued from the remaining interventional period of the study.

If the specified discontinuation criteria for the zibotentan 5 mg monotherapy arm are not met at the interim analysis at 6 weeks of treatment, the available Part A data will undergo a second interim analysis to assess changes in fluid-related measures when all randomised Part A participants have completed 12 weeks of treatment. If fluid-related measures meet the specified criteria in at least 5 participants in the zibotentan 5 mg monotherapy arm at the second interim analysis (at 12 weeks of treatment), this arm will be discontinued from the remaining interventional period of the study.

In Part B, an additional 528 eligible participants are planned to be recruited. Of these, 352 participants will be randomised into the same 4 treatment arms from Part A of 88 participants each. The remaining eligible participants will be randomised into 2 additional treatment arms of 88 participants each:

Zibotentan 0.25 mg+Dapagliflozin 10 mg once daily.
Zibotentan 1.5 mg+Dapagliflozin 10 mg once daily.
Zibotentan 5 mg+Dapagliflozin 10 mg once daily.
Zibotentan 5 mg once daily.
Dapagliflozin 10 mg once daily.
Placebo once daily.

Participants randomised in Part A cannot be randomised in Part B.

Participants will be stratified by diabetes (DKD versus non-DM CKD) and baseline eGFR (below versus above 45 mL/min/1.73m2) at the time of randomisation to ensure an approximate balance between treatment groups within each sub-population. The number of randomised participants in each stratum will be monitored to ensure the non-DM CKD subpopulation is approximately a minimum of 30% and a maximum of 33% of the total number of participants randomised.

For each participant, the total duration of participation will be approximately 17 to 19 weeks. In each study part, the screening period can be up to 4 weeks in duration prior to randomisation. The first dose will be taken after randomisation at the baseline visit on Day 1. In addition to the baseline visit, the participant will visit the clinic 5 times during the following 12 weeks of treatment. Approximately 2 weeks after the last dose, the participant will visit the clinic again for a follow-up assessment.

Objectives and Endpoints

The primary endpoint will measure the effect on zibotentan and dapagliflozin in combination and alone versus placebo on UACR. The change in UACR will be measured in log transformed UACR (UACR (mg/g)=urine albumin (mg/dL)/urine creatinine (g/dL)) from baseline to week 12. The secondary endpoints and objectives are summarized in Table 17 below.

TABLE 17

Secondary Endpoints and Additional Objectives of the ZENITH-CKD Ph2b trial

| Objective | Endpoint Description |
|---|---|
| To determine the change in UACR for doses of zibotentan combined with 10 mg dapagliflozin versus 10 mg dapagliflozin alone | Change in log-transformed UACR from baseline to Week 12. |
| To determine the change in office systolic and diastolic BP for doses of zibotentan combined with 10 mg dapagliflozin and for zibotentan and 10 mg dapagliflozin alone versus placebo. | Change in BP from baseline (Visit 2) to Week 12. |
| To characterise the dose-response relationship (relationship between different doses of zibotentan/a fixed dose of dapagliflozin and UACR reduction). | The least squares mean change of UACR at Week 12 from the 3 Zibo/Dapa dose groups and the dapagliflozin monotherapy group |
| To determine the effect of ranging doses of zibotentan and dapagliflozin in combination and alone on eGFR. | Change in eGFR from baseline to Week 1. Change in eGFR from baseline to Week 12. Change in eGFR from baseline to Week 14. Change in eGFR from Week 1 to Week 12. |
| To assess the safety and tolerability of ranging doses of zibotentan and dapagliflozin in combination and alone versus placebo | AEs/SAEs/DAEs. Vital signs. Clinical laboratory tests. 12-lead ECG assessment. Event of special interest (changes in fluid-related measures). |
| To assess the pharmacokinetics of ranging doses of zibotentan and dapagliflozin in plasma. | Plasma concentrations of zibotentan and dapagliflozin. |
| Exploratory analysis of zibotentan metabolites (Part B only). | Plasma concentration of zibotentan metabolites. |
| To assess placebo-corrected body weight changes in response to ranging doses of zibotentan and dapagliflozin in combination and alone. | Change in body weight throughout the interventional period. |
| To explore the relationships between zibotentan dose/exposure and safety/PD variables | Dose/exposure of zibotentan relative to safety and PD variables. Safety/PD variables include blood assessment for NT-proBNP, BNP, creatinine, and cystatin C, and urine assessment of albumin and creatinine. |

TABLE 17-continued

Secondary Endpoints and Additional Objectives of the ZENITH-CKD Ph2b trial

| Objective | Endpoint Description |
| --- | --- |
| To assess the effect of zibotentan and dapagliflozin in combination and alone versus placebo on plasma/serum K+, Na+, uric acid, BUN, fasting plasma glucose, haematocrit, haemoglobin, ET-1, ELDR, CT-proET-1, and copeptin levels. | Change in plasma/serum concentrations of K+, Na+, uric acid, BUN, fasting plasma glucose, haematocrit, haemoglobin, ET-1, ELDR, CT-proET-1, and copeptin levels over time during the study. |
| To assess the effect of zibotentan and dapagliflozin in combination and alone versus placebo on cardiovascular biomarkers in blood | Evaluation of changes in cardiovascular biomarkers in blood over time during the study. |
| To assess the effect of zibotentan and dapagliflozin in combination and alone versus placebo on body fluid volume and distribution status. | Evaluation of changes in body fluid volume and distribution over the time course of the study. Change in total body water, extracellular water and intracellular water volumes. Results will be obtained from using bioimpedance spectroscopy. |
| To collect and store plasma, serum, and urine samples for potential future exploratory research aimed at exploring biomarkers involved in PK, PD, safety and tolerability related to zibotentan and dapagliflozin in combination and alone versus placebo or related to cardiorenal diseases. | Evaluation of changes in blood and urine biomarkers relevant to cardiorenal mechanisms, inflammation, and fibrosis over the time course of the study. |

The invention claimed is:

1. A method of reducing UACR and reducing the incidence of cardiovascular or renal death in a human patient with chronic kidney disease, the method comprising administering to the patient in need thereof, a combination of zibotentan, N-(3-methoxy-5-methylpyrazin-2-yl)-2-[4-(1,3,4-oxadiazol-2-yl)phenyl]pyridine-3-sulfonamide,

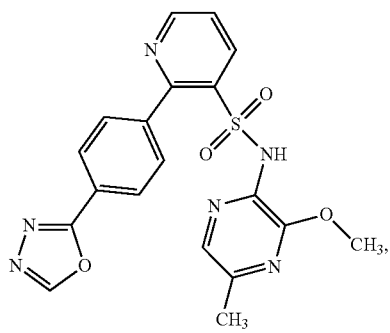

I or a pharmaceutically acceptable salt thereof, and dapagliflozin.

2. The method according to claim 1, where zibotentan, or a pharmaceutically acceptable salt thereof, is administered once daily in combination with dapagliflozin.

3. The method according to claim 2, where zibotentan, or a pharmaceutically acceptable salt thereof, is administered at a dose of about 5 mg and dapagliflozin is administered at a dose of 10 mg.

4. The method according to claim 2, where zibotentan, or a pharmaceutically acceptable salt thereof, is administered at a dose of about 1.5 mg and dapagliflozin is administered at a dose of 10 mg.

5. The method according to claim 2, where zibotentan, or a pharmaceutically acceptable salt thereof, is administered at a dose of about 0.25 mg and dapagliflozin is administered at a dose of 10 mg.

6. The method according to claim 2, wherein the patient is a chronic kidney disease patient classified as a stage 1-4 patient having an eGFR 20-60 ml/min/1.73 m$^2$.

7. The method according to claim 6, wherein the human patient is a chronic kidney disease patient classified as a stage 3-4 patient.

8. A method of reducing UACR to <300 mg/g in a human patient with chronic kidney disease, the method comprising administering to the patient in need thereof, a combination of zibotentan, N-(3-methoxy-5-methylpyrazin-2-yl)-2-[4-(1,3,4-oxadiazol-2-yl)phenyl]pyridine-3-sulfonamide,

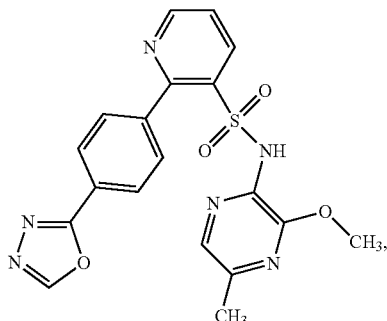

or a pharmaceutically acceptable salt thereof, and dapagliflozin.

9. The method according to claim 8, where zibotentan, or a pharmaceutically acceptable salt thereof, is administered once daily in combination with dapagliflozin.

10. The method according to claim 9, where zibotentan, or a pharmaceutically acceptable salt thereof, is administered at a dose of about 5 mg and dapagliflozin is administered at a dose of 10 mg.

11. The method according to claim 9, where zibotentan, or a pharmaceutically acceptable salt thereof, is administered at a dose of about 1.5 mg and dapagliflozin is administered at a dose of 10 mg.

12. The method according to claim 9, where zibotentan, or a pharmaceutically acceptable salt thereof, is administered at a dose of about 0.25 mg and dapagliflozin is administered at a dose of 10 mg.

13. The method according to claim 9, wherein the patient is a chronic kidney disease patient classified as a stage 1-4 patient having an eGFR 20-60 ml/min/1.73 m$^2$.

14. The method according to claim 13, wherein the human patient is a chronic kidney disease patient classified as a stage 3-4 patient.

15. A method of reducing the risk of UACR progressing to ≥3000 mg/g in a human patient with chronic kidney disease, the method comprising administering to the patient in need thereof, a combination of zibotentan, N-(3-methoxy-5-methylpyrazin-2-yl)-2-[4-(1,3,4-oxadiazol-2-yl)phenyl]pyridine-3-sulfonamide,

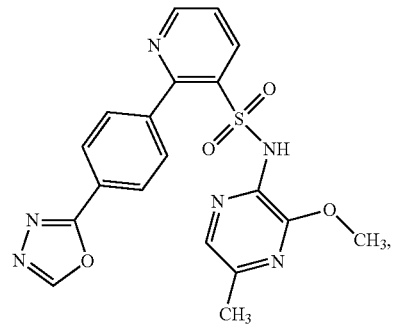

or a pharmaceutically acceptable salt thereof, and dapagliflozin.

16. The method according to claim 15, where zibotentan, or a pharmaceutically acceptable salt thereof, is administered once daily in combination with dapagliflozin.

17. The method according to claim 16, where zibotentan, or a pharmaceutically acceptable salt thereof, is administered at a dose of about 5 mg and dapagliflozin is administered at a dose of 10 mg.

18. The method according to claim 16, where zibotentan, or a pharmaceutically acceptable salt thereof, is administered at a dose of about 1.5 mg and dapagliflozin is administered at a dose of 10 mg.

19. The method according to claim 16, where zibotentan, or a pharmaceutically acceptable salt thereof, is administered at a dose of about 0.25 mg and dapagliflozin is administered at a dose of 10 mg.

20. The method according to claim 16, wherein the patient is a chronic kidney disease patient classified as a stage 1-4 patient having an eGFR 20-60 ml/min/1.73 m$^2$.

21. The method according to claim 20, wherein the human patient is a chronic kidney disease patient classified as a stage 3-4 patient.

\* \* \* \* \*